US010355256B2

(12) United States Patent
Kashu et al.

(10) Patent No.: US 10,355,256 B2
(45) Date of Patent: Jul. 16, 2019

(54) FILM PRODUCTION METHOD AND FILM PRODUCTION DEVICE

(71) Applicant: Sumitomo Chemical Company, Limited, Tokyo (JP)

(72) Inventors: Koji Kashu, Niihama (JP); Yusuke Kon, Daegu (KR); Tatsuya Sakamoto, Niihama (JP); Jian Wang, Daegu (KR)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/517,729

(22) PCT Filed: Sep. 18, 2015

(86) PCT No.: PCT/JP2015/076651
§ 371 (c)(1),
(2) Date: Apr. 7, 2017

(87) PCT Pub. No.: WO2016/056379
PCT Pub. Date: Apr. 14, 2016

(65) Prior Publication Data
US 2017/0317327 A1 Nov. 2, 2017

(30) Foreign Application Priority Data

Oct. 10, 2014 (JP) .................... 2014-209414
Jan. 30, 2015 (WO) .................. PCT/JP2015/052749

(51) Int. Cl.
*B26D 1/03* (2006.01)
*H01M 2/14* (2006.01)
(Continued)

(52) U.S. Cl.
CPC ............ *H01M 2/145* (2013.01); *B26D 1/035* (2013.01); *B26D 7/14* (2013.01); *B26D 7/2614* (2013.01);
(Continued)

(58) Field of Classification Search
CPC ........ B26D 1/035; B26D 7/14; B26D 7/2614; H01M 2/145; B65H 16/10; B65H 18/08; G01N 21/892; G01N 21/894
See application file for complete search history.

(56) References Cited

U.S. PATENT DOCUMENTS 3,806,015 A * 4/1974 Kachioff ................ G01N 27/82
226/33
5,523,848 A 6/1996 Musso et al.
(Continued)

FOREIGN PATENT DOCUMENTS

CN 1804601 A 7/2006
CN 1873398 A 12/2006
(Continued)

OTHER PUBLICATIONS

Office Action dated Sep. 25, 2017 in CN Application No. 201580054773.
(Continued)

*Primary Examiner* — Kenneth E Peterson
*Assistant Examiner* — Liang Dong
(74) *Attorney, Agent, or Firm* — Panitch Schwarze Belisario & Nadel LLP

(57) ABSTRACT

A method of film production includes the steps of obtaining defect information including information on the position of a defect (D) in a separator original sheet (12*b*), slitting the separator original sheet (12*b*) to produce a plurality of separators (12*a*), and determining, on the basis of the defect information on a single defect (D), that a separator (12*a*) actually having the defect (D) and another separator (12*a*) adjacent to the above separator (12*a*) are defective.

15 Claims, 17 Drawing Sheets

(51) Int. Cl.

| | | |
|---|---|---|
| *G01N 21/892* | (2006.01) | |
| *G01N 21/894* | (2006.01) | |
| *H01M 10/0525* | (2010.01) | |
| *H01M 2/16* | (2006.01) | |
| *B65H 18/08* | (2006.01) | |
| *B65H 16/10* | (2006.01) | |
| *B26D 7/26* | (2006.01) | |
| *B26D 7/14* | (2006.01) | |
| *B65H 26/02* | (2006.01) | |
| *G03B 1/04* | (2006.01) | |
| *G03B 21/32* | (2006.01) | |
| *G03B 17/42* | (2006.01) | |
| *G03B 1/56* | (2006.01) | |
| *G03B 1/42* | (2006.01) | |
| *G03B 17/30* | (2006.01) | |
| *G01N 21/84* | (2006.01) | |
| *G03B 21/00* | (2006.01) | |
| *G03B 17/00* | (2006.01) | |

(52) U.S. Cl.
CPC ............. *B65H 16/10* (2013.01); *B65H 18/08* (2013.01); *B65H 26/02* (2013.01); *G01N 21/8422* (2013.01); *G01N 21/892* (2013.01); *G01N 21/894* (2013.01); *G03B 1/04* (2013.01); *G03B 1/42* (2013.01); *G03B 1/56* (2013.01); *G03B 17/30* (2013.01); *G03B 17/425* (2013.01); *G03B 21/328* (2013.01); *H01M 2/1653* (2013.01); *H01M 2/1686* (2013.01); *H01M 10/0525* (2013.01); *B65H 2557/62* (2013.01); *G03B 17/00* (2013.01); *G03B 21/00* (2013.01); *G03B 2217/243* (2013.01); *H01M 2/166* (2013.01)

(56) References Cited

U.S. PATENT DOCUMENTS

| | | |
|---|---|---|
| 6,219,930 B1 | 4/2001 | Reid |
| 2002/0139273 A1 | 10/2002 | Murata et al. |
| 2004/0251176 A1 | 12/2004 | Alonso et al. |
| 2006/0164647 A1 | 7/2006 | Shibata |
| 2008/0087149 A1 | 4/2008 | Ohashi |
| 2010/0294418 A1 | 11/2010 | Yura et al. |
| 2011/0085125 A1 | 4/2011 | Kimura et al. |
| 2011/0159347 A1 | 6/2011 | Shibano et al. |
| 2012/0002153 A1 | 1/2012 | Kimura et al. |
| 2012/0002154 A1 | 1/2012 | Kimura et al. |
| 2012/0028067 A1 | 2/2012 | Izaki et al. |
| 2012/0055607 A1 | 3/2012 | Kitagawa et al. |
| 2012/0055608 A1 | 3/2012 | Kitagawa et al. |
| 2012/0055621 A1 | 3/2012 | Goto et al. |
| 2012/0055622 A1 | 3/2012 | Kitagawa et al. |
| 2012/0055623 A1 | 3/2012 | Kitagawa et al. |
| 2012/0056211 A1 | 3/2012 | Kitagawa et al. |
| 2012/0056340 A1 | 3/2012 | Kitagawa et al. |
| 2012/0057104 A1 | 3/2012 | Kitagawa et al. |
| 2012/0057107 A1 | 3/2012 | Kitagawa et al. |
| 2012/0057231 A1 | 3/2012 | Goto et al. |
| 2012/0057232 A1 | 3/2012 | Goto et al. |
| 2012/0058291 A1 | 3/2012 | Kitagawa et al. |
| 2012/0058321 A1 | 3/2012 | Goto et al. |
| 2013/0100529 A1 | 4/2013 | Kitagawa et al. |
| 2013/0114139 A1 | 5/2013 | Kitagawa et al. |
| 2013/0169956 A1 | 7/2013 | Cano Cediel et al. |
| 2014/0014762 A1 | 1/2014 | Ichinomiya et al. |
| 2014/0186568 A1 | 7/2014 | Kitagawa et al. |
| 2014/0287255 A1 | 9/2014 | Izaki et al. |
| 2015/0183199 A1 | 7/2015 | Kitagawa et al. |
| 2016/0054494 A1 | 2/2016 | Kitagawa et al. |
| 2016/0103258 A1 | 4/2016 | Kitagawa et al. |
| 2016/0377416 A1 | 12/2016 | Reid et al. |
| 2017/0317327 A1 | 11/2017 | Kashu et al. |

FOREIGN PATENT DOCUMENTS

| | | |
|---|---|---|
| CN | 101468543 A | 7/2009 |
| CN | 101925944 A | 12/2010 |
| CN | 101980797 A | 2/2011 |
| CN | 101981438 A | 2/2011 |
| CN | 102043280 A | 5/2011 |
| CN | 102160212 A | 8/2011 |
| CN | 102341733 A | 2/2012 |
| CN | 102385086 A | 3/2012 |
| CN | 102385087 A | 3/2012 |
| CN | 202562855 U | 11/2012 |
| CN | 102866168 A | 1/2013 |
| JP | H8101130 A | 4/1996 |
| JP | 2002228429 A | 8/2002 |
| JP | 2004338406 A | 12/2004 |
| JP | 2004338409 A | 12/2004 |
| JP | 2006194721 A | 7/2006 |
| JP | 2006220527 A | 8/2006 |
| JP | 200882910 A | 4/2008 |
| JP | 2008116437 A | 5/2008 |
| JP | 2009133741 A | 6/2009 |
| JP | 2009244063 A | 10/2009 |
| JP | 201032346 A | 2/2010 |
| JP | 2011220967 A | 11/2011 |
| JP | 201333033 A | 2/2013 |

OTHER PUBLICATIONS

Office Action dated Oct. 10, 2017 in CN Application No. 201580054771.1.

Office Action dated Dec. 11, 2017 in U.S. Appl. No. 15/517,199, by Kashu.

Office Action dated Nov. 28, 2017 in CN Application No. 201580056172.3.

Int'l Preliminary Report on Patentability dated Apr. 20, 2017 in Int'l Application No. PCT/JP2015/076652.

Int'l Preliminary Report on Patentability dated Apr. 20, 2017 in Int'l Application No. PCT/JP2015/076651.

Int'l Preliminary Report on Patentability dated Apr. 20, 2017 in Int'l Application No. PCT/JP2015/076650.

Int'l Preliminary Report on Patentability dated Apr. 20, 2017 in Int'l Application No. PCT/JP2015/052749.

Office Action dated Apr. 7, 2015 in JP Application No. 2015-506030 (Partial Translation).

Int'l Search Report dated Dec. 8, 2015 in In'l Application No. PCT/JP2015/076652.

Int'l Search Report dated Dec. 8, 2015 in Int'l Application No. PCT/JP2015/076651.

Int'l Search Report dated Dec. 8, 2015 in Int'l Application No. PCT/JP2015/076650.

Int'l Search Report dated Apr. 14, 2015 in In'l Application No. PCT/JP2015/052749.

Office Action dated Jun. 14, 2016 in JP Application No. 2016-520128.

Decision to Grant dated Sep. 6, 2016 in JP Application No. 2016-520128.

Office Action dated Jun. 14, 2016 in JP Application No. 2016-520129.

Decision to Grant dated Sep. 6, 2016 in JP Application No. 2016-520129.

Office Action dated Jun. 14, 2016 in JP Application No. 2016-520115.

Decision to Grant dated Sep. 6, 2016 in JP Application No. 2016-520115.

Office Action dated Jan. 8, 2018 in U.S. Appl. No. 15/517,818, by Kashu.

Office Action dated Feb. 11, 2018 in CN Application No. 201580054773.0.

Office Action dated Sep. 19, 2018 in U.S. Appl. No. 15/517,249 by Watanabe.

(56) References Cited

OTHER PUBLICATIONS

Office Action dated Dec. 24, 2018 in CN Application No. 201580054791.9.

* cited by examiner

FILM PRODUCTION METHOD AND FILM PRODUCTION DEVICE

CROSS-REFERENCE TO RELATED APPLICATION

This application is a Section 371 of International Application No. PCT/JP2015/076651, filed Sep. 18, 2015, which was published in the Japanese language on Apr. 14, 2016 under International Publication No. WO 2016/056379 A1, and the disclosure of which is incorporated herein by reference.

TECHNICAL FIELD

The present invention relates to a film producing method, a film producing apparatus, a film, and a film roll.

BACKGROUND ART

There has been known a deficiency inspecting device for a sheet-shaped product including an optical film (Patent Literature 1). The deficiency inspecting device receives information on a deficiency from a protective film inspecting section, and forms a data code (for example, a two-dimensional code or a QR Code [registered trademark]) having a fixed pitch and indicative of the deficiency. The deficiency inspecting device forms such a data code on a surface at an end of a PVA film original sheet together with information on the position and production identification.

With the above arrangement, obtaining information on the position of a deficiency in a sheet-shaped product makes it possible to specify which film has the deficiency among a plurality of films prepared by cutting the sheet-shaped product lengthwise in a slitting step. Subsequently carrying out an appropriate measure for any deficient film, for example, cutting off a deficient portion, allows for production of a film having no deficiency.

CITATION LIST

Patent Literature

[Patent Literature 1] Japanese Patent Application Publication, Tokukai, No. 2008-116437 (Publication date: May 22, 2008)

SUMMARY OF INVENTION

Technical Problem

Even in a case where information has been obtained on the position of a defect in a sheet-shaped product as an original sheet of a film (hereinafter referred to as "film original sheet"), it will be impossible to accurately specify which film has the defect among a plurality of films, if the film original sheet was not cut at desired slit positions during the slitting step. In such cases, a defective film will unfortunately be determined as non-defective. This will result in a failure to take an appropriate measure for a defective film, possibly letting such a defective film be publicly available as if it were a non-defective film.

It is an object of an embodiment of the present invention to provide a film producing method, a film producing apparatus, a film, and a film roll each of which involves a reduced risk of, in a case where a film original sheet is cut for film production, erroneously determining that a film is non-defective when it is actually defective.

Solution to Problem

In order to attain the above object, a film producing method in accordance with an embodiment of the present invention includes the steps of: (a) obtaining defect information including information on a position of a defect in a film original sheet; (b) slitting the film original sheet along a slit line, extending in a longitudinal direction of the film original sheet, so as to produce a plurality of films; and (c) carrying out defectiveness determination for the plurality of films on a basis of the defect information so as to determine that a film out of the plurality of films which film actually has the defect and a film out of the plurality of films which film is adjacent to the film actually having the defect are each a defective film.

With the above production method, carrying out defectiveness determination for films produced through the slitting step leads to determining that not only a film actually having a defect but also another film adjacent to the film having the defect is defective. With this arrangement, even in a case where a film original sheet has been slit at positions different from desired slit positions, so that a defect is not present in a first film in which the defect would otherwise be present and that the defect is present in a second film different from and adjacent to the first film, it is possible to reduce the risk of erroneously determining that a film is non-defective when it is actually defective.

The film producing method in accordance with an embodiment of the present invention may be arranged such that in the step (a), the defect information indicates presence or absence of defectiveness in each of a plurality of divisional regions arranged on a surface of the film original sheet in a width direction of the film original sheet; and in the step (c), on the basis of the defect information on a single divisional region out of the plurality of divisional regions which single divisional region has the defect, a film including the single divisional region and a film adjacent to the film including the single divisional region are each determined as a defective film.

The above production method includes obtaining information on the presence or absence of defectiveness for each divisional region of a film original sheet and determining that a film adjacent to a film actually having a defect is also defective. The above production method, as described above, includes determining on the basis of simple information on the presence or absence of defectiveness for each divisional region that the adjacent film is defective. This makes it possible to reduce the risk of erroneously determining that a film is non-defective when it is actually defective.

The film producing method in accordance with an embodiment of the present invention may be arranged such that in the step (b), the slit line extends on a boundary line between the plurality of divisional regions; and in the step (c), the film adjacent to the film including the single divisional region includes a divisional region out of the plurality of divisional regions which divisional region is adjacent to the single divisional region via a boundary line between the single divisional region and the divisional region adjacent to the single divisional region.

In a case where a film original sheet is slit along a slit line extending on a boundary line of a divisional region having a defect, displacement of the slit position likely results in a defect being in a film that is different from and adjacent to a film in which the defect would otherwise be present.

The above production method includes slitting a film original sheet along a slit line extending on a boundary line of each divisional region and determining that a film including a divisional region adjacent to a divisional region having a defect is also defective. This makes it possible to appropriately determine that a film likely to have a defect as a result of displacement of slit positions is defective, and to reduce the risk of erroneously determining that a film is non-defective when it is actually defective.

The film producing method in accordance with an embodiment of the present invention may be arranged such that in the step (b), the film original sheet is slit along the slit line, which extends on the boundary line between the plurality of divisional regions, in such a manner that the plurality of films correspond respectively to the plurality of divisional regions; and in the step (c), the film adjacent to the film including the single divisional region includes a divisional region out of the plurality of divisional regions, corresponding respectively to the plurality of films, which divisional region is adjacent to a divisional region out of the plurality of divisional regions, which divisional region has the defect and is positioned at an end among the plurality of divisional regions, via a boundary line between the divisional region having the defect and the divisional region adjacent to the divisional region having the defect.

In a case where a film original sheet is slit in such a manner that each film corresponds to a single divisional region, a defect is likely to be present in either of the films on respective opposite sides of a film corresponding to a divisional region having the defect. This makes it necessary to determine that such films on the respective opposite sides are defective.

In contrast, the above production method includes slitting a film original sheet in such a manner that the films produced correspond respectively to the plurality of divisional regions. A defect is thus unlikely to be present in at least one of the films on the respective opposite sides of a film corresponding to a divisional region having a defect. This eliminates the need to determine that the at least one film is a defective film. This in turn makes it possible to reduce the number of films that are determined as defective even though they actually have no defect.

The film producing method in accordance with an embodiment of the present invention may be arranged such that in the step (b), the film original sheet is slit along the slit line, which extends on the boundary line between the plurality of divisional regions, in such a manner that the plurality of films each correspond to three of the plurality of divisional regions; and in the step (c), the film adjacent to the film including the single divisional region includes a divisional region out of the three of the plurality of divisional regions, corresponding respectively to the plurality of films, which divisional region is adjacent to a divisional region out of the three of the plurality of divisional regions, which divisional region has the defect and is positioned at an end among the three of the plurality of divisional regions, via a boundary line between the divisional region having the defect and the divisional region adjacent to the divisional region having the defect.

With the above production method, in a case where a defect is present in a middle divisional region among the three divisional regions corresponding to a single film, the defect is unlikely to be present in either of the films on the respective opposite sides of the film corresponding to the three divisional regions. This eliminates the need to determine that such films on the respective opposite sides are defective. This in turn makes it possible to reduce the number of films that are determined as defective even though they actually have no defect.

The film producing method in accordance with an embodiment of the present invention may be arranged such that in the step (b), the slit line divides one of the plurality of divisional regions; and in the step (c), two films each including a divisional part of the single divisional region are each determined as a defective film.

In a case where a film original sheet is slit along a slit line dividing a divisional region, two films each including a divisional part of a divisional region having a defect are both likely to have the defect. The above production method makes it possible to determine that such two films likely to have a defect are defective. This makes it possible to reduce the risk of erroneously determining that a film is non-defective when it is actually defective.

The film producing method in accordance with an embodiment of the present invention may be arranged such that in the step (a), the defect information indicates presence or absence of defectiveness in each of first divisional regions and second divisional regions, which are wider than the first divisional regions, that are arranged alternately; in the step (b), the slit line divides one of the first divisional regions; and in the step (c), two films each including a divisional part of the at least one first divisional region are each determined as a defective film.

In a case where two films each including a divisional part of a divisional region having a defect are determined as defective, dividing a narrow divisional region, rather than dividing a wide divisional region, less likely results in a defect being present in a divisional part of the divisional region. This makes it possible to reduce the number of films that are determined as defective even though they actually have no defect.

In order to attain the above object, a film producing method in accordance with an embodiment of the present invention includes the steps of: (a) obtaining defect information including information on a position of a defect in a film original sheet; (b) slitting the film original sheet along a slit line, extending in a longitudinal direction of the film original sheet, so as to produce a plurality of films; and (c) carrying out defectiveness determination for the plurality of films on a basis of the defect information, in the step (a), the defect information indicating presence or absence of defectiveness in each of a plurality of divisional regions arranged on a surface of the film original sheet in a width direction of the film original sheet, in the step (c), in a case where the slit line does not extend through a divisional region out of the plurality of divisional regions which divisional region has the defect, a single film including the divisional region having the defect being determined as a defective film, and in a case where the slit line extends through the divisional region having the defect or on a boundary line of the divisional region having the defect, two films produced by slitting the film original sheet along the slit line being each determined as a defective film.

With the above production method, in a case where the slit line extends through the divisional region having the defect or on a boundary line of the divisional region having the defect, two films produced by slitting the film original sheet along the slit line are each determined as a defective film. In a case where a film original sheet is slit along a slit line extending through a divisional region having a defect, displacement of the slit position likely results in a defect being in a film that is different from and adjacent to a film in which the defect would otherwise be present. Determining that two films sandwiching a slit line and adjacent to each other are defective makes it possible to, even in a case where a defect is not present in a first film in which the defect would otherwise be present and the defect is present in a second film different from and adjacent to the first film, reduce the risk of erroneously determining that a film is non-defective when it is actually defective.

Further, with the above production method, in a case where the slit line does not extend through a divisional region having a defect, a single film including the divisional region having the defect is determined as defective. In a case where a divisional region having a defect is not slit along a slit line, displacement of the slit position does not likely result in a defect being in a film that is different from and adjacent to a film in which the defect would otherwise be present. Thus, determining a single film including a divisional region having a defect as defective makes it possible to reduce the number of films that are determined as defective even though they actually have no defect.

The film producing method in accordance with an embodiment of the present invention may further include the step of recording the defect information for each unit region having a predetermined length in the longitudinal direction of the film original sheet.

The above production method makes it possible to, in a case where there are a plurality of defects in a unit region, record all defect information for each unit region and thus simplify the production process.

The film producing method in accordance with an embodiment of the present invention may be arranged such that in the step of recording the defect information, information on the presence or absence of defectiveness for each of the plurality of divisional regions in the unit region is recorded.

The above production method makes it possible to record all information on the presence or absence of defectiveness for each divisional region of the unit region and thus reduce the amount of information to be recorded.

The film producing method in accordance with an embodiment of the present invention may be arranged such that in the step of recording the defect information, in correspondence with the number of defects in the unit region, switching is carried out between a first mode, in which the defect information recorded is at least one information item selected from the group consisting of (i) information on the number of defects in the unit region, (ii) information on a position of each of the defects, and (iii) information on a size of each of the defects, and a second mode, in which the defect information recorded is the information on the presence or absence of defectiveness for each of the plurality of divisional regions in the unit region.

The above production method makes it possible to switch in correspondence with the number of defects between the first mode, in which detailed defect information is recorded, and the second mode, in which simple information is recorded. Thus, in a case where there is a restriction on the amount of information that can be recorded, it is possible to record defect information suitable under that restriction.

The film producing method in accordance with an embodiment of the present invention may further include the step of providing (i) the film actually having the defect with a first marking indicative of the position of the defect and (ii) the film adjacent to the film actually having the defect with a second marking at a position corresponding to the first marking.

The above production method makes it possible to easily sense the position of a defect in a defective film during a later step.

The film producing method in accordance with an embodiment of the present invention may further include the step of, on the basis of the defect information, providing the film original sheet with (i) a first marking at a position corresponding to the film actually having the defect, the first marking indicating the position of the defect, and with (ii) a second marking at a position that corresponds to the film adjacent to the film actually having the defect and that is as shifted from the position of the first marking in the width direction, wherein in the step (b), the film original sheet provided with the first marking and the second marking is slit.

The above production method, which includes providing a marking to a film original sheet before the slitting step, makes it possible to provide a marking at a correct position in comparison to a case of providing a marking to an individual film after the slitting step.

The film producing method in accordance with an embodiment of the present invention may be arranged such that in the step of the providing, the first marking and the second marking are so provided as not to coincide with the slit line.

The above production method makes it possible to prevent a situation in which markings have been cut during the slitting step and it is consequently difficult to determine whether a film is defective.

The film producing method in accordance with an embodiment of the present invention may further include the step of cutting off a portion of the defective film on the basis of the defect information.

The above production method makes it possible to cut off a defective portion from a defective film to use the remainder as a non-defective film.

In order to attain the above object, a film producing apparatus in accordance with an embodiment of the present invention includes: a defect information obtaining section configured to obtain defect information including information on a position of a defect in a film original sheet; a slitting section configured to slit the film original sheet along a slit line, extending in a longitudinal direction of the film original sheet, so as to produce a plurality of films; and a determining section configured to carry out defectiveness determination for the plurality of films on a basis of the defect information so as to determine that a film out of the plurality of films which film actually has the defect and a film out of the plurality of films which film is adjacent to the film actually having the defect are each a defective film.

In order to attain the above object, a film producing apparatus in accordance with an embodiment of the present invention includes: a defect information obtaining section configured to obtain defect information including information on a position of a defect in a film original sheet; a slitting section configured to slit the film original sheet along a slit line, extending in a longitudinal direction of the film original sheet, so as to produce a plurality of films; and a determining section configured to carry out defectiveness determination for the plurality of films on a basis of the defect information, the defect information obtaining section obtaining the defect information indicating presence or absence of defectiveness in each of a plurality of divisional regions arranged on a surface of the film original sheet in a width direction of the film original sheet, the determining section being configured such that in a case where the slit line does not extend through a divisional region having a defect, a single film including the divisional region having the defect is determined as a defective film, and in a case where the slit line extends through the divisional region having the defect or on a boundary line of the divisional region having the defect, two films produced by slitting the film original sheet along the slit line are each determined as a defective film.

In order to attain the above object, a film in accordance with an embodiment of the present invention is one of a plurality of films corresponding respectively to a plurality of regions on a surface of a film original sheet having a defect which plurality of regions are defined by a boundary line extending in a longitudinal direction of the film original sheet, the film corresponding to a region out of the plurality of regions which region is adjacent, via the boundary line, to a region out of the plurality of regions which region has the defect, the film being provided with a marking at a position opposite to the defect across the boundary line.

In order to attain the above object, a film roll in accordance with an embodiment of the present invention includes the film having been rolled up in a roll shape.

Rolling up a film into a film roll while the film is provided with a marking at a position corresponding to a defect as described above makes it possible to easily handle the film and also to recognize the position of the defect when the film is wound off.

Advantageous Effects of Invention

An embodiment of the present invention makes it possible to provide a film producing method, a film producing apparatus, a film, and a film roll each of which reduces the possibility of, in a case where a film original sheet is cut for film production, making a defective film publicly available.

DESCRIPTION OF EMBODIMENTS

The following description will discuss embodiments of the present invention in detail.

Embodiment 1

The description below deals with, as an example film in accordance with an embodiment of the present invention, a separator and a heat-resistant separator for a battery such as a lithium-ion secondary battery. The description below further deals in order with a separator producing method and a separator producing apparatus as an example of a film producing method and a film producing apparatus in accordance with an embodiment of the present invention.

<Lithium-Ion Secondary Battery>

A nonaqueous electrolyte secondary battery, typically a lithium-ion secondary battery, has a high energy density, and is therefore currently widely used not only as batteries for use in devices such as personal computers, mobile phones, and mobile information terminals, and for use in moving bodies such as automobiles and airplanes, but also as stationary batteries contributing to stable power supply.

Figure 1:
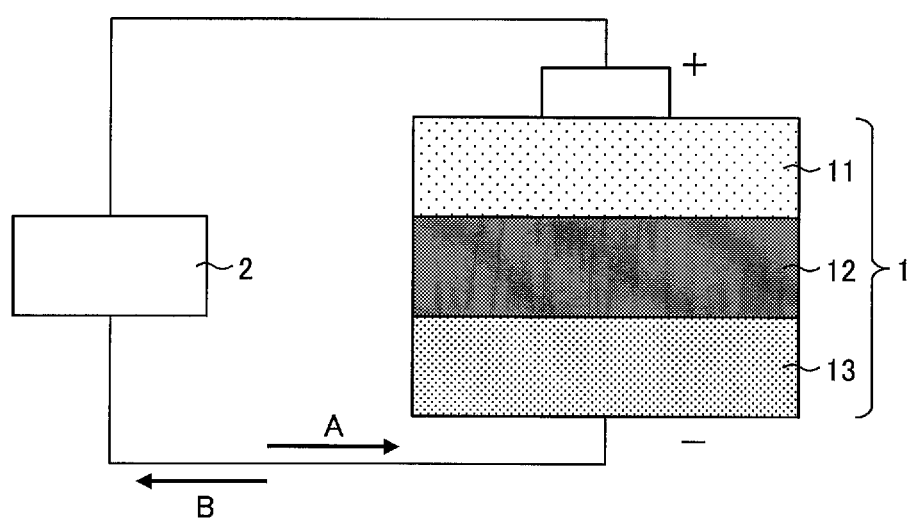
FIG. 1 is a diagram schematically illustrating a cross-sectional configuration of a lithium-ion secondary battery in accordance with Embodiment 1.

FIG. 1 is a diagram schematically illustrating a cross-sectional configuration of a lithium-ion secondary battery 1. As illustrated in FIG. 1, the lithium-ion secondary battery 1 includes a cathode 11, a separator 12, and an anode 13. Between the cathode 11 and the anode 13, an external device 2 is connected outside the lithium-ion secondary battery 1. While the lithium-ion secondary battery 1 is being charged, electrons move in a direction A. Meanwhile, while the lithium-ion secondary battery 1 is being discharged, electrons move in a direction B.

<Separator>

The separator 12 is provided so as to be sandwiched between the cathode 11 (as a positive electrode) and the anode 13 (as a negative electrode) of the lithium-ion secondary battery 1. While separating the cathode 11 and the anode 13, the separator 12, which is a porous film, allows lithium ions to move between the cathode 11 and the anode 13. The separator 12 contains, for example, a polyolefin (for example, polyethylene or polypropylene) as a material thereof.

Figure 2:
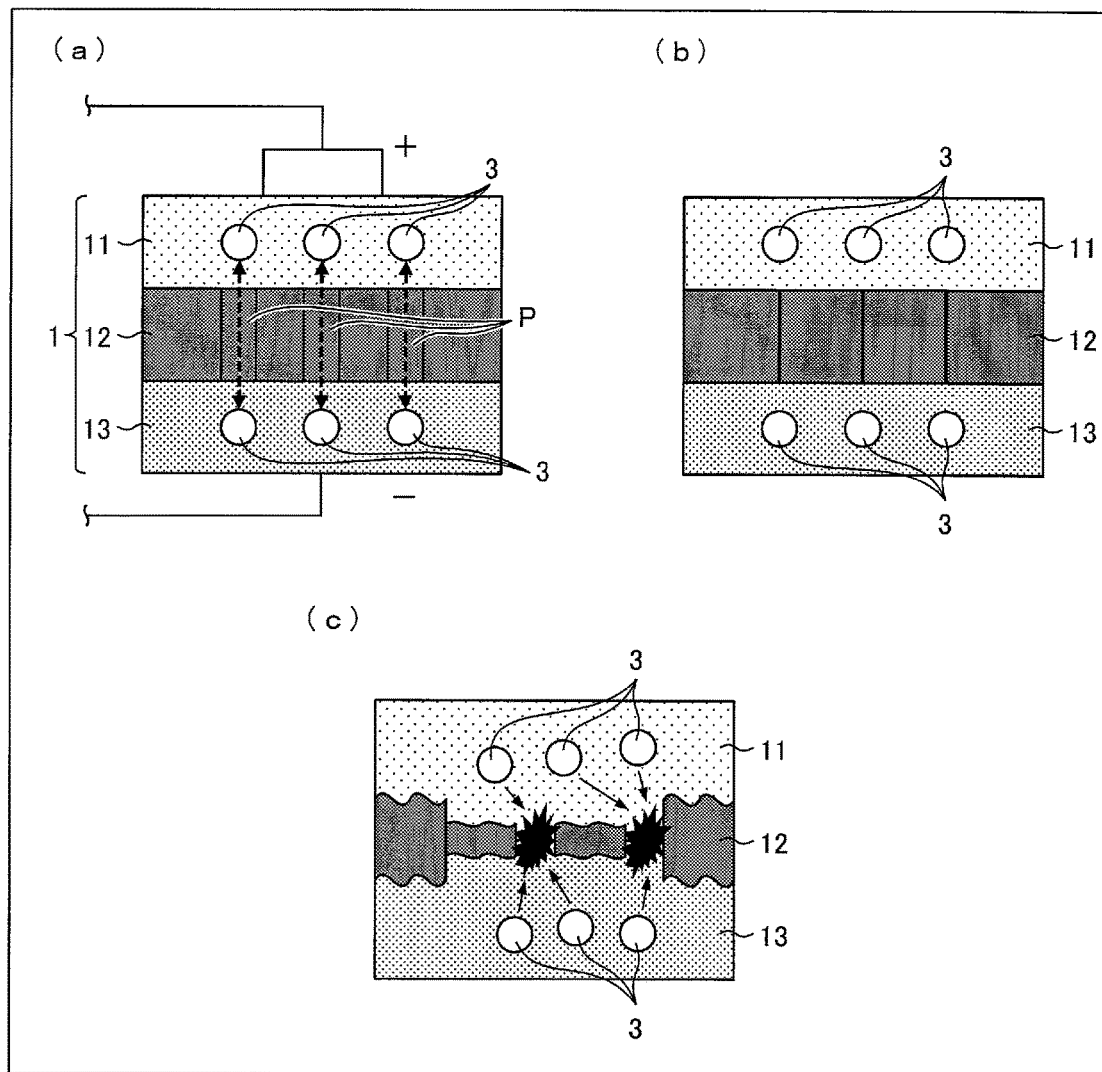
FIG. 2 provides diagrams schematically illustrating details of the configuration of the lithium-ion secondary battery illustrated in FIG. 1.

FIG. 2 provides diagrams schematically illustrating details of the configuration of the lithium-ion secondary battery 1 illustrated in FIG. 1. (a) of FIG. 2 illustrates a normal configuration. (b) of FIG. 2 illustrates a state in which the temperature of the lithium-ion secondary battery 1 has risen. (c) of FIG. 2 illustrates a state in which the temperature of the lithium-ion secondary battery 1 has sharply risen.

As illustrated in (a) of FIG. 2, the separator 12 is provided with many pores P. Normally, lithium ions 3 in the lithium-ion secondary battery 1 can move back and forth through the pores P.

Note here that there may be, for example, a case where the lithium-ion secondary battery 1 increases in temperature due to, for example, (i) overcharge of the lithium-ion secondary battery 1 or (ii) a large current caused by a short circuit having occurred in an external device. In such cases, the separator 12 melts or softens and the pores P are blocked as illustrated in (b) of FIG. 2. As a result, the separator 12 shrinks. This stops the movement of the lithium ions 3, and consequently stops the increase in temperature (described earlier).

Note, however, that the separator 12 suddenly shrinks in a case where the lithium-ion secondary battery 1 sharply increases in temperature. In this case, as illustrated in (c) of FIG. 2, the separator 12 may be broken. Then, the lithium ions 3 leak out from the separator 12 which has been broken, so that the lithium ions 3 do not stop moving back and forth. Thus, the increase in temperature continues.

<Heat-Resistant Separator>

Figure 3:
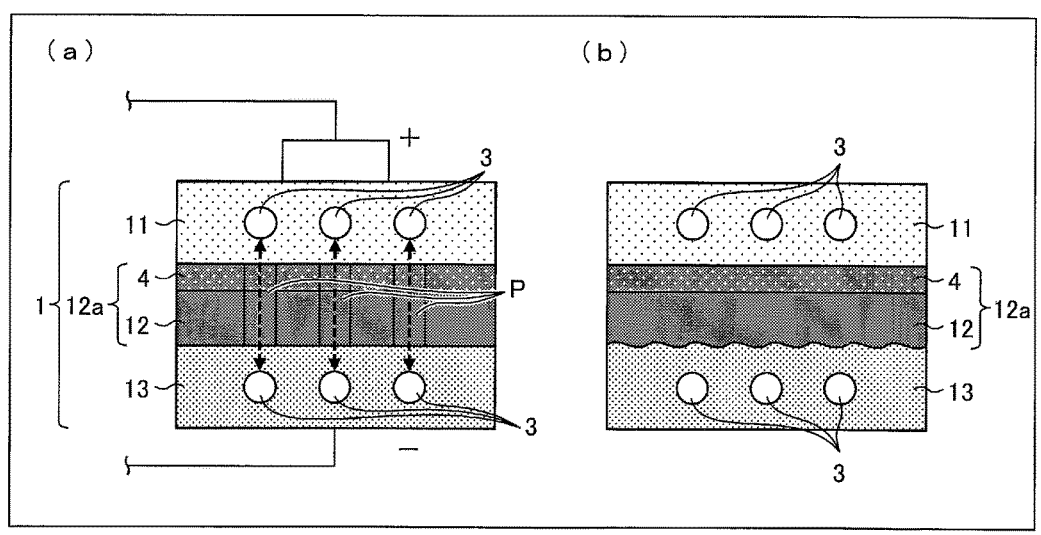
FIG. 3 provides diagrams schematically illustrating another configuration of the lithium-ion secondary battery illustrated in FIG. 1.

FIG. 3 provides diagrams schematically illustrating another configuration of the lithium-ion secondary battery 1 illustrated in FIG. 1. (a) of FIG. 3 illustrates a normal configuration, and (b) of FIG. 3 illustrates a state in which the temperature of the lithium-ion secondary battery 1 has sharply risen.

As illustrated in (a) of FIG. 3, the lithium-ion secondary battery 1 can further include a heat-resistant layer 4. The heat-resistant layer 4 and the separator 12 form a heat-resistant separator 12a (separator). The heat-resistant layer 4 is laminated on one surface of the separator 12 which surface is on the cathode 11 side. The heat-resistant layer 4 may alternatively be laminated on (i) a surface of the separator 12 which surface is on the anode 13 side or on (ii) both surfaces of the separator 12. Further, the heat-resistant layer 4 is provided with pores that are similar to the pores P. Normally, lithium ions 3 move back and forth through the pores P and the pores of the heat-resistant layer 4. The heat-resistant layer 4 contains, for example, wholly aromatic polyamide (aramid resin) as a material thereof.

As illustrated in (b) of FIG. 3, even in a case where the temperature of the lithium-ion secondary battery 1 has sharply risen and accordingly the separator 12 has melted or softened, the shape of the separator 12 is maintained because the heat-resistant layer 4 supports the separator 12. Thus, such a sharp increase in temperature merely results in melting or softening of the separator 12 and consequent blocking of the pores P. This stops the movement of the lithium ions 3, and consequently stops overdischarge and overcharge (described earlier). The separator 12 is thus prevented from being broken.

<Steps of Producing Heat-Resistant Separator Original Sheet (Separator Original Sheet)>

How to produce the heat-resistant separator 12a of the lithium-ion secondary battery 1 is not particularly limited. The heat-resistant separator 12a can be produced by a publicly known method. The following discussion assumes a case where the separator 12 contains polyethylene as a main material. However, even in a case where the separator 12 contains another material, the similar steps can still be applied to production of the heat-resistant separator 12a.

For example, it is possible to employ a method including the steps of first forming a film by adding an inorganic filler or plasticizer to a thermoplastic resin, and then removing the inorganic filler or plasticizer with an appropriate solvent. For example, in a case where the separator 12 is a polyolefin separator made of a polyethylene resin containing an ultra-high molecular weight polyethylene, it is possible to produce a separator 12 by the following method.

This method includes (1) a kneading step of obtaining a polyethylene resin composition by kneading an ultrahigh molecular weight polyethylene with an inorganic filler (for example, calcium carbonate or silica) or plasticizer (for example, a low-molecular weight polyolefin or liquid paraffin), (2) a rolling step of forming a film from the polyethylene resin composition, (3) a removal step of removing the inorganic filler or plasticizer from the film obtained in the step (2), and (4) a stretching step of obtaining a separator 12 by stretching the film obtained in the step (3). The step (4) can alternatively be carried out between the steps (2) and (3).

In the removal step, many fine pores are provided in the film. The fine pores of the film stretched in the stretching step become the above-described pores P. The separator 12 formed as a result is a polyethylene microporous film having a prescribed thickness and a prescribed air permeability.

Note that the kneading step may involve kneading (i) 100 parts by weight of the ultrahigh molecular weight polyethylene, (ii) 5 parts by weight to 200 parts by weight of a low-molecular weight polyolefin having a weight-average molecular weight of 10000 or less, and (iii) 100 parts by weight to 400 parts by weight of the inorganic filler.

Thereafter, in a coating step, the heat-resistant layer 4 is formed on a surface of the separator 12. For example, on the separator 12, an aramid/NMP (N-methylpyrrolidone) solution (coating solution) is applied, and thereby, the heat-resistant layer 4 that is an aramid heat-resistant layer is formed. The heat-resistant layer 4 can be provided on only one surface or both surfaces of the separator 12. Alternatively, the heat-resistant layer 4 can be formed by using, for coating, a mixed solution containing a filler such as alumina/carboxymethyl cellulose.

Further, in the coating step, a polyvinylidene fluoride/dimethylacetamide solution (coating solution) can be applied (applying step) to a surface of the separator 12 and solidified (solidifying step) so that an adhesive layer is formed on the surface of the separator 12. The adhesive layer can be provided on only one surface or both surfaces of the separator 12.

A method for coating the separator 12 with a coating solution is not particularly limited as long as uniform wet coating can be performed by the method. The method can be a conventionally well-known method such as a capillary coating method, a spin coating method, a slit die coating method, a spray coating method, a dip coating method, a roll coating method, a screen printing method, a flexo printing method, a bar coater method, a gravure coater method, or a die coater method. The heat-resistant layer 4 has a thickness which can be controlled by adjusting (i) the thickness of a coating wet film, (ii) the solid-content concentration (which is the sum of concentrations of a binder and a filler in the coating solution), and/or (iii) the ratio of the filler to the binder.

It is possible to use a resin film, a metal belt, a drum or the like as a support with which the separator 12 is fixed or transferred in coating.

Figure 4:
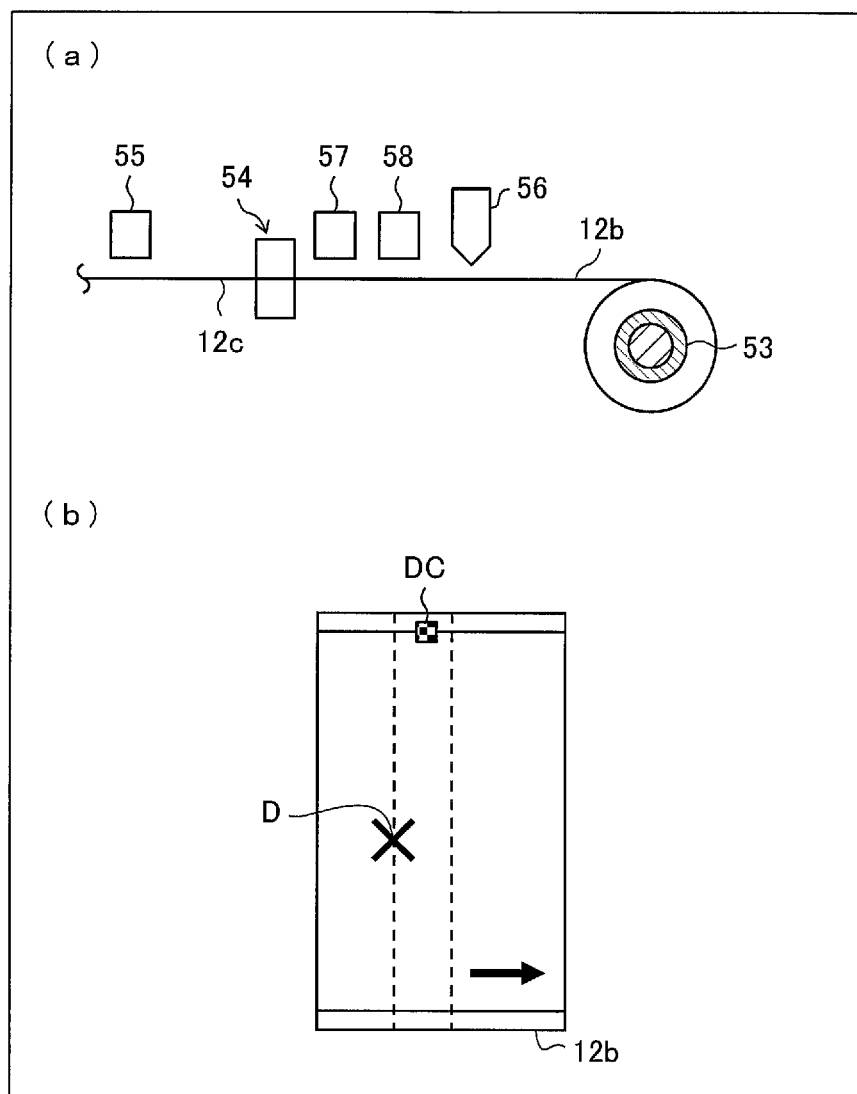
FIG. 4 provides diagrams schematically illustrating a defect detecting step and a defect information recording step both included in a method for marking a defect in a separator original sheet.

This operation allows for production of a heat-resistant separator original sheet 12b which is a separator original sheet 12c on which the heat-resistant layer 4 is laminated (see FIG. 4). The heat-resistant separator original sheet 12b thus produced is wound around a core 53 having a cylindrical shape (see FIG. 4). Note that the subject to be produced by the above production method is not limited to the heat-resistant separator original sheet 12b. The above production method does not necessarily include the coating step. In this case, the subject to be produced is a separator original sheet 12c. The description below mainly deals with an example of a heat-resistant separator (film) including a heat-resistant layer as a functional layer. A similar process (steps) can be carried out also for a separator (film) and separator original sheet (film original sheet) each including no functional layer.

<Defect Detecting Step>

In a case where during production of a heat-resistant separator for use in a lithium-ion secondary battery, an inspecting device has detected a defect in a coating step of preparing a heat-resistant separator original sheet including a separator original sheet coated with a heat-resistant layer, the original sheet having the defect is provided with a line drawn with a marker before the heat-resistant separator original sheet is wound up. In the subsequent slitting step, the heat-resistant separator original sheet is wound off. Then, when an operator sees the line drawn with the marker on the heat-resistant separator original sheet wound off, the operator stops the operation of winding off the heat-resistant separator original sheet. Next, the operator visually checks the position, along the width of the heat-resistant separator original sheet, of the defect indicated by the line drawn with the marker. Next, that portion of the heat-resistant separator original sheet on which the line is drawn with the marker is slit by a cutting device lengthwise to form a plurality of heat-resistant separators. Then, the operator attaches, to one of the heat-resistant separators, a piece of tape in such a manner that (i) the tape coincides with the lengthwise position on the heat-resistant separator at which position the defect indicated by the line drawn with the marker is present and that (ii) the tape extends beyond a side of the heat-resistant separator. The heat-resistant separator, to which the tape is attached in such a manner that the tape extends beyond a side of the heat-resistant separator, is wound up around a wind-up roller.

Next, the heat-resistant separator wound up around the wind-up roller is wound off from the wind-up roller and then wound up around an additional wind-up roller in an additional wind-up step. When an operator sees the tape in the additional wind-up step, the operator stops the operation of the additional wind-up step. The operator then cuts off, in the width direction, that portion of the heat-resistant separator at which the defect indicated by the tape is present, and removes that portion from the rest. Next, the heat-resistant separator on the side of the wind-up roller is connected with the heat-resistant separator on the side of the additional wind-up roller. Then, the operation of the additional wind-up step is resumed, so that the heat-resistant separator is all wound off from the wind-up roller and then wound up around the additional wind-up roller.

This procedure is, however, problematic in that it merely involves drawing a line on a heat-resistant separator original sheet with a marker in a case where an inspecting device has detected a defect in the heat-resistant separator original sheet. Thus, when an operator sees the line in the subsequent slitting step, the operator needs to stop the operation of winding off the heat-resistant separator original sheet and visually check the widthwise position of the defect. Enormous efforts are thus needed in order to specify the position of the defect in a plurality of heat-resistant separators prepared by slitting the heat-resistant separator original sheet.

Figure 5:
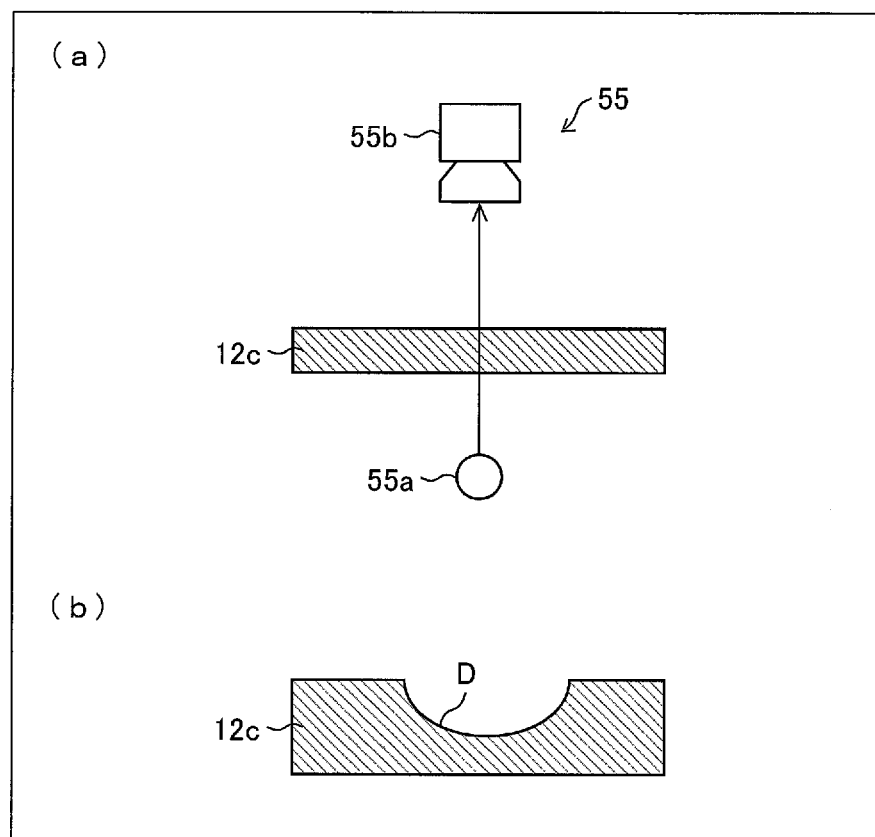
FIG. 5 provides diagrams illustrating a configuration of a base material defect inspecting device in the defect detecting step.
Figure 6:
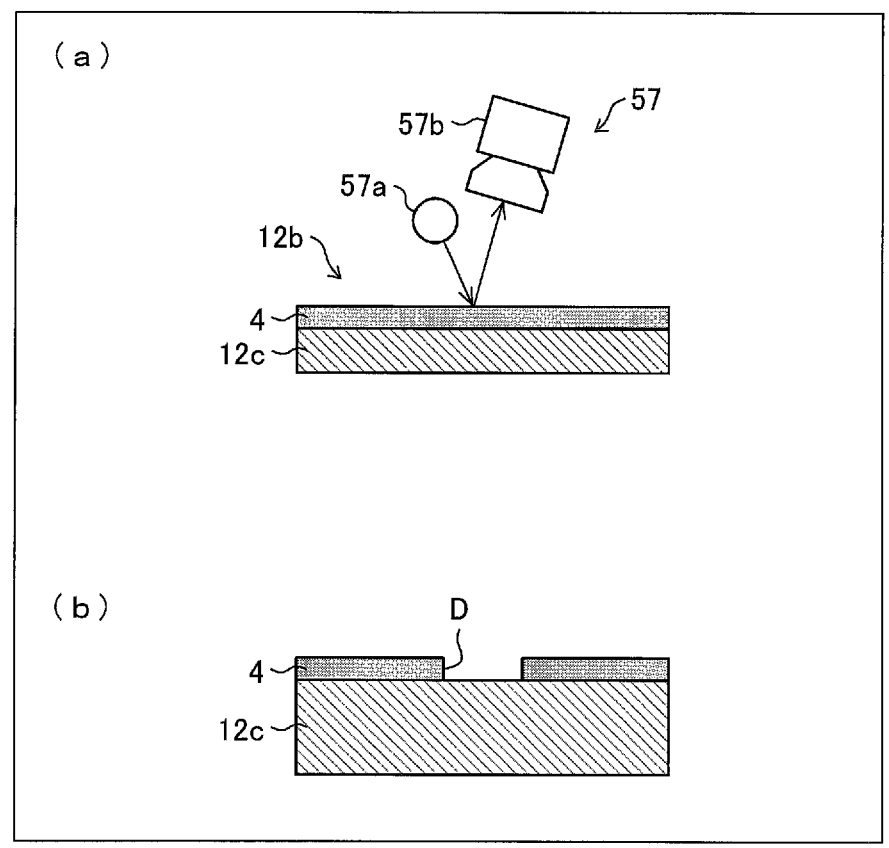
FIG. 6 provides diagrams illustrating a configuration of a coating defect inspecting device in the defect detecting step.
Figure 7:
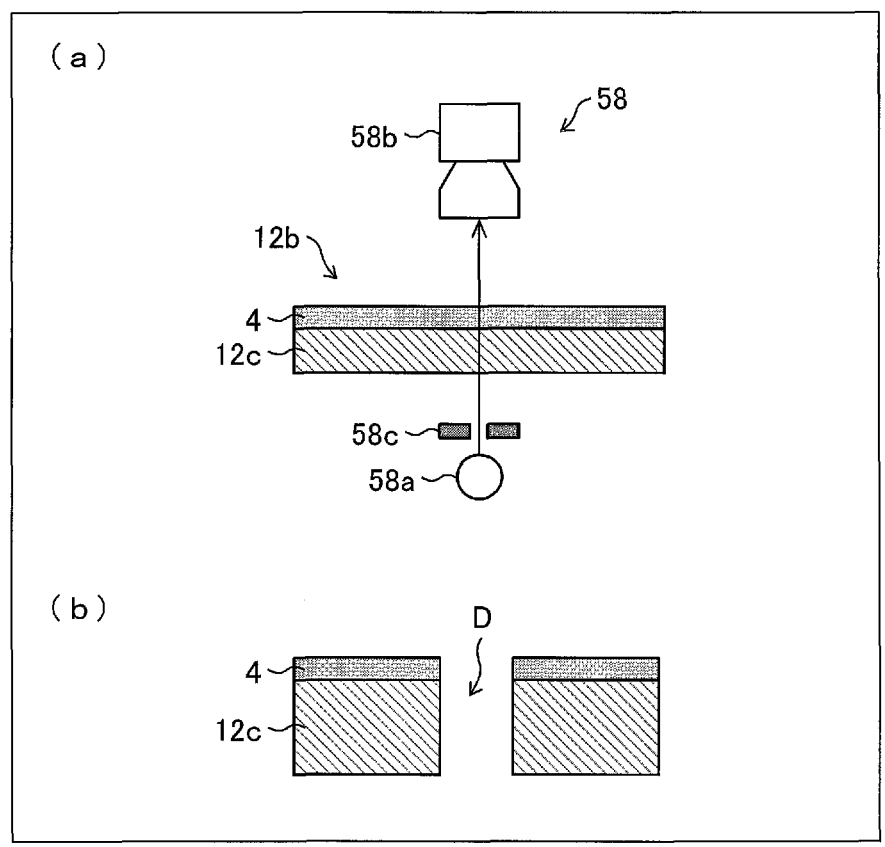
FIG. 7 provides diagrams illustrating a configuration of a pinhole defect inspecting device in the defect detecting step.

FIG. 4 provides diagrams schematically illustrating a defect detecting step and a defect information recording step both included in a method for marking a defect in the heat-resistant separator original sheet 12b. (a) of FIG. 4 is an elevational view of the two steps, whereas (b) of FIG. 4 is a plan view of the two steps. FIG. 5 provides diagrams illustrating a configuration of a base material defect inspecting device 55 in the defect detecting step. FIG. 6 provides diagrams illustrating a configuration of a coating defect inspecting device 57 in the defect detecting step. FIG. 7 provides diagrams illustrating a configuration of a pinhole defect inspecting device 58 in the defect detecting step.

A heat-resistant layer is formed on a separator original sheet 12c by the coating section 54 so that a heat-resistant separator original sheet 12b is prepared. The heat-resistant separator original sheet 12b is wound up around a core 53. Specifically, a base material inspecting step (defect detecting step) is a step of inspecting the separator original sheet 12c for a defect D. The base material inspecting step is carried out by a base material defect inspecting device 55 (defect detecting section, separator producing apparatus) between a step of unreeling the separator original sheet 12c and the coating step. The base material defect inspecting device 55 includes a light source 55a and a detector 55b that are so positioned as to sandwich the separator original sheet 12c. The light source 55a emits light in a direction perpendicular to the front and back surfaces of the separator original sheet 12c, whereas the detector 55b detects light having passed through the separator original sheet 12c. This allows the base material defect inspecting device 55 to inspect the separator original sheet 12c for a defect D present therein, that is, specify the position of a defect D (defect detecting step). The defect D present in the separator original sheet 12c is, for example, a through hole (pinhole), an inappropriate film thickness, or a defect caused by a foreign substance.

A coating inspecting step (defect detecting step) is a step of inspecting the heat-resistant layer 4, formed on the separator original sheet 12c, for a defect D. The coating inspecting step is carried out by a coating defect inspecting device 57 (defect detecting section, separator producing apparatus) between the coating step and a step of winding up the heat-resistant separator original sheet 12b around the core 53. The coating defect inspecting device 57 includes a light source 57a and a detector 57b that are positioned on the side of the heat-resistant layer 4 of the heat-resistant separator original sheet 12b. The light source 57a emits light to the heat-resistant layer 4, whereas the detector 57b detects light having been reflected by the heat-resistant layer 4. This allows the coating defect inspecting device 57 to detect a defect D present in the heat-resistant layer 4 (that is, specify the position of a defect D). The defect D present in the heat-resistant layer 4 is, for example, a crease, peeling off, repellency, and a surface failure. The repellency refers to a defect of a foreign substance, oil, or the like on the surface of the separator original sheet 12c repelling the coating solution from the surface, with the result of local absence of a heat-resistant layer 4 or local formation of an extremely thin heat-resistant layer 4. The surface failure refers to a failure in the thickness of the heat-resistant layer 4.

A pinhole inspecting step (defect detecting step) is a step of inspecting the heat-resistant separator original sheet 12b for a defect D in the form of a pinhole. The pinhole inspecting step is carried out by a pinhole defect inspecting device 58 (defect detecting section, separator producing apparatus) positioned between the coating defect inspecting device 57 and a defect information recording device 56. The pinhole defect inspecting device 58 includes a light source 58a, a detector 58b, and a slit 58c. The light source 58a is positioned on the side of the separator original sheet 12c of the heat-resistant separator original sheet 12b, and emits light in a direction perpendicular to the front and back surfaces of the heat-resistant separator original sheet 12b. The slit 58c lets the light pass therethrough and travel toward the heat-resistant separator original sheet 12b. The detector 58b detects a defect D (that is, specifies the position of a defect D) on the basis of light having passed through the heat-resistant separator original sheet 12b. The defect D in the form of a pinhole has a diameter ranging from several hundreds of micrometers to several millimeters.

The production process involves a defect information recording device 56 positioned between the pinhole defect inspecting device 58 and the core 53. The defect information recording device 56 records, on the heat-resistant separator original sheet 12b, a defect code DC indicative of defect information such as information on the position of any defect D detected by the base material defect inspecting device 55, the coating defect inspecting device 57, or the pinhole defect inspecting device 58. The defect information recording device 56 records such a defect code DC at a portion on a widthwise side of the heat-resistant separator original sheet 12b which portion corresponds to the lengthwise position of the defect D on the heat-resistant separator original sheet 12b. The defect code DC may be code data such as a two-dimensional code or QR Code (registered trademark). The information on the position indicates where the defect D is positioned in the longitudinal and width directions of the heat-resistant separator original sheet 12b. The information on the position may include information with which the type of the defect D is distinguishable. The type of a defect D is, for example, (i) a structural defect in the base material for which defect the base material defect inspecting device 55 inspects the separator original sheet 12c, (ii) a defect caused in the applying step for which defect the coating defect inspecting device 57 inspects the heat-resistant layer 4, or (iii) a defect in the form of an opening for which defect the pinhole defect inspecting device 58 inspects the heat-resistant separator original sheet 12b.

The separator original sheet 12c or heat-resistant separator original sheet 12b is subjected to a film tension of typically not more than 200 N/m, preferably not more than 120 N/m. The term "film tension" refers to a tension applied to a film being conveyed, the tension being applied in the conveying direction over a unit widthwise length of the film. For instance, with a film tension of 200 N/m, a force of 200 N is applied to the film over a width of 1 m. A film tension of more than 200 N/m may form a wrinkle in the conveying direction of the film and decrease the accuracy of defect inspection. The film tension is typically not less than 10 N/m, preferably not less than 30 N/m. A film tension of less than 10 N/m may cause slack in the film or let the film meander. The separator original sheet 12c or heat-resistant separator original sheet 12b has pores P, and is subjected to a film tension lower than a film tension applied to a non-porous film such as an optical film. The separator original sheet 12c or heat-resistant separator original sheet 12b thus has a physical property of being stretchable more easily than a non-porous film such as an optical film. As such, in a case where a defect code DC is recorded at a portion on a widthwise side of the heat-resistant separator original sheet 12b which portion corresponds to the lengthwise position of the defect D on the heat-resistant separator original sheet 12b, the lengthwise position of the defect D is substantially not displaced from the lengthwise position of the defect code DC even in a case where the heat-resistant separator original sheet 12b has been stretched lengthwise. The lengthwise position of a defect D is thus easily specifiable even in the case where the heat-resistant separator original sheet 12b has been stretched lengthwise.

The heat-resistant separator original sheet 12b with a defect code DC recorded at a portion on a widthwise side thereof is wound up around the core 53. The core 53, around which the heat-resistant separator original sheet 12b has been wound up, is carried to a position for the subsequent slitting step.

The defect information recording device 56 (see FIG. 4) records a defect code DC indicative of information on the position of a defect D at a portion on a widthwise side of the heat-resistant separator original sheet 12b which portion corresponds to the lengthwise position of the defect D on the heat-resistant separator original sheet 12b. A defect D is separated from its corresponding defect code DC by a lengthwise distance $L_{MD}$ of, for example, preferably not more than 100 mm, more preferably not more than 30 mm. The defect code DC is separated from a widthwise side of the heat-resistant separator original sheet 12b by a distance LTD of, for example, preferably not more than 100 mm, more preferably not more than 30 mm. The distance LTD is preferably not less than 10 mm because the widthwise sides of the heat-resistant separator original sheet 12b easily become wavy.

<Slitting Apparatus>

The heat-resistant separator 12a (hereinafter referred to as "separator"), produced from the heat-resistant separator original sheet 12b (hereinafter referred to as "separator original sheet"), or the separator 12, produced from the separator original sheet 12c, has a width (hereinafter referred to as "product width") suitable for application products such as the lithium-ion secondary battery 1. For improved productivity, however, the separator original sheet is produced so as to have a width that is equal to or larger than a product width. Then, after having been once produced so as to have a width equal to or larger than the product width, the separator original sheet is cut (slit) into a separator(s) having the product width.

Note that the expression "width of a/the separator" means a dimension of the separator in a direction that is parallel to a plane in which the separator extends and that is perpendicular to the longitudinal direction of the separator. Moreover, "slit" means to cut off a separator original sheet lengthwise (i.e., in a direction in which a film flows in production, MD: machine direction), whereas "cut" means to cut the separator original sheet or separator in a transverse direction (TD). The transverse direction (TD) means a direction (widthwise direction) that is substantially perpendicular to the lengthwise direction (MD) and the thickness direction of the separator.

Figure 8:
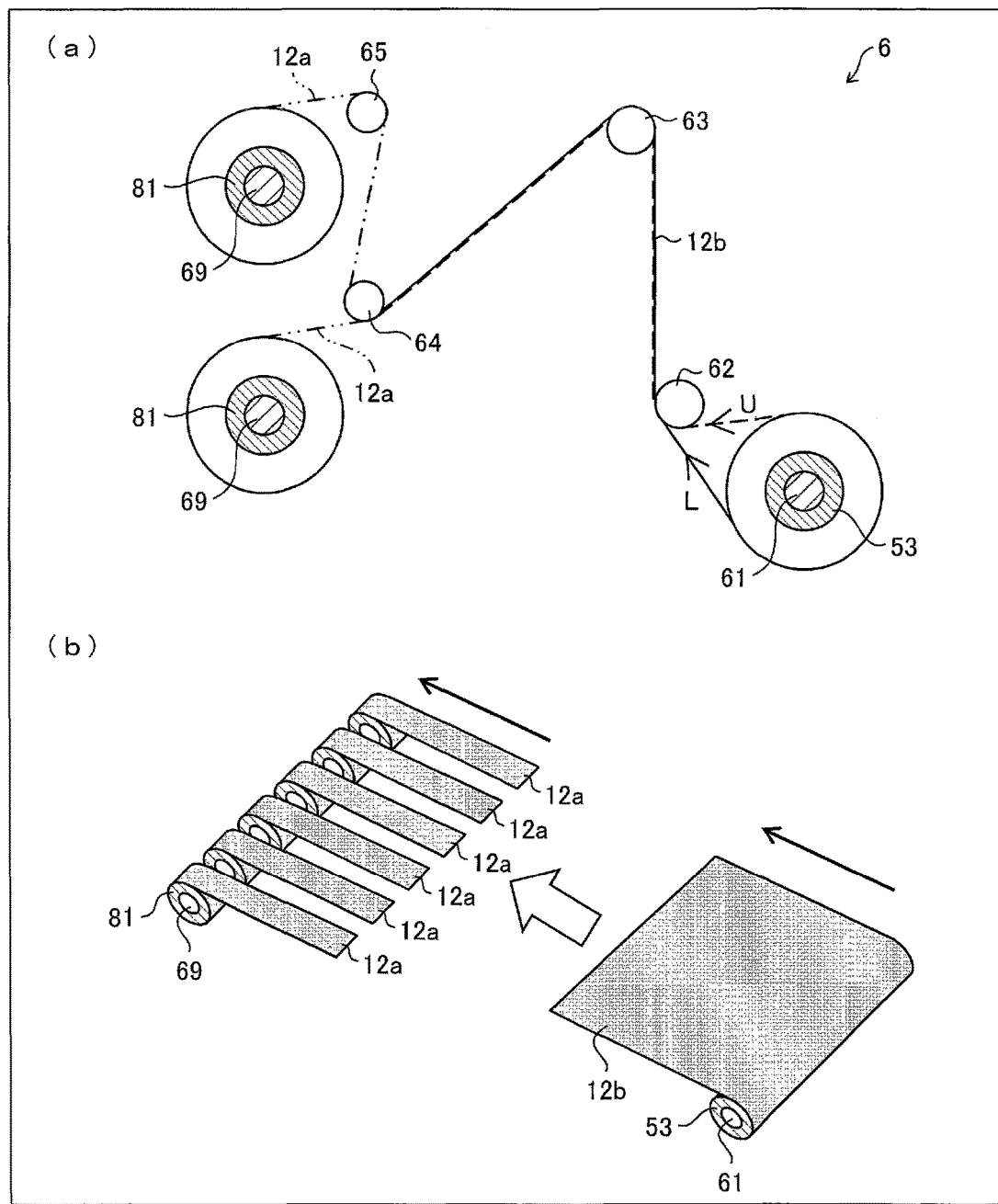
FIG. 8 provides diagrams schematically illustrating a configuration of a slitting apparatus configured to slit a separator.

FIG. 8 provides diagrams schematically illustrating a configuration of a slitting apparatus 6 configured to slit the separator original sheet 12b. (a) of FIG. 8 illustrates the entire configuration, and (b) of FIG. 8 illustrates an arrangement before and after slitting the separator original sheet 12b.

As illustrated in (a) of FIG. 8, the slitting apparatus 6 includes a rotatably supported cylindrical wind-off roller 61, rollers 62 to 65, and wind-up rollers 69. The slitting apparatus 6 is further provided with a cutting device 7 (see FIG. 9) described later.

<Before Slitting>

In the slitting apparatus 6, a cylindrical core 53 on which the separator original sheet 12b is wrapped is fit on the wind-off roller 61. As illustrated in (a) of FIG. 8, the separator original sheet 12b is wound off from the core 53 to a route U or L. The separator original sheet 12b thus wound off is conveyed to the roller 64 via the roller 63 at a speed of, for example, 100 m/min. In the conveying step, the separator original sheet 12b is slit lengthwise into a plurality of separators 12a.

<After Slitting>

As illustrated in (a) of FIG. 8, one or more of the plurality of separators 12a are wound up around respective cores 81 (bobbins) fit on the plurality of wind-up rollers 69. Further, another one or more of the plurality of separators 12a are wound up around respective cores 81 (bobbins) fit on the plurality of wind-up rollers 69. Note that each of the slit separators wound into a roll form is referred to as a "separator roll (film roll)".

<Cutting Device>

Figure 9:
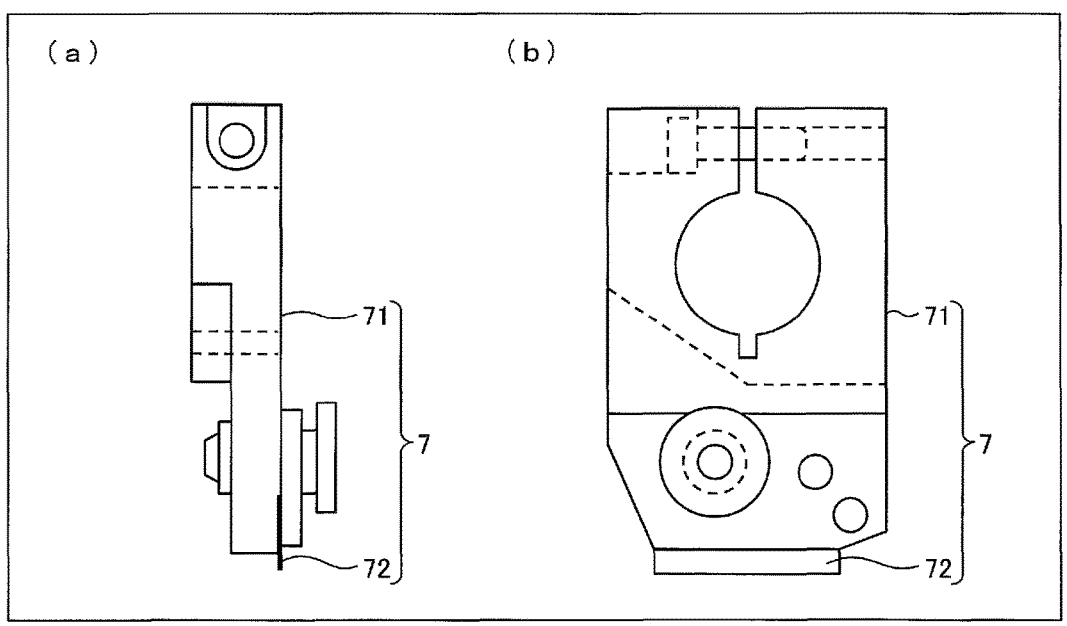
FIG. 9 provides an enlarged view, a side view, and an elevational view of a cutting device included in the slitting apparatus illustrated in FIG. 8.

FIG. 9 provides views each illustrating a configuration of the cutting device 7 (slitting section) of the slitting apparatus 6 illustrated in (a) of FIG. 8. (a) of FIG. 9 is a side view of the cutting device 7, and (b) of FIG. 9 is an elevational view of the cutting device 7.

As illustrated in (a) and (b) of FIG. 9, the cutting device 7 includes a holder 71 and a blade 72. The holder 71 is fixed to a housing or the like provided in the slitting apparatus 6. The holder 71 holds the blade 72 in such a manner that the blade 72 and the separator original sheet 12b being conveyed have a fixed positional relation. The blade 72 has a finely sharpened edge and slits the separator original sheet by using this edge.

Figure 10:
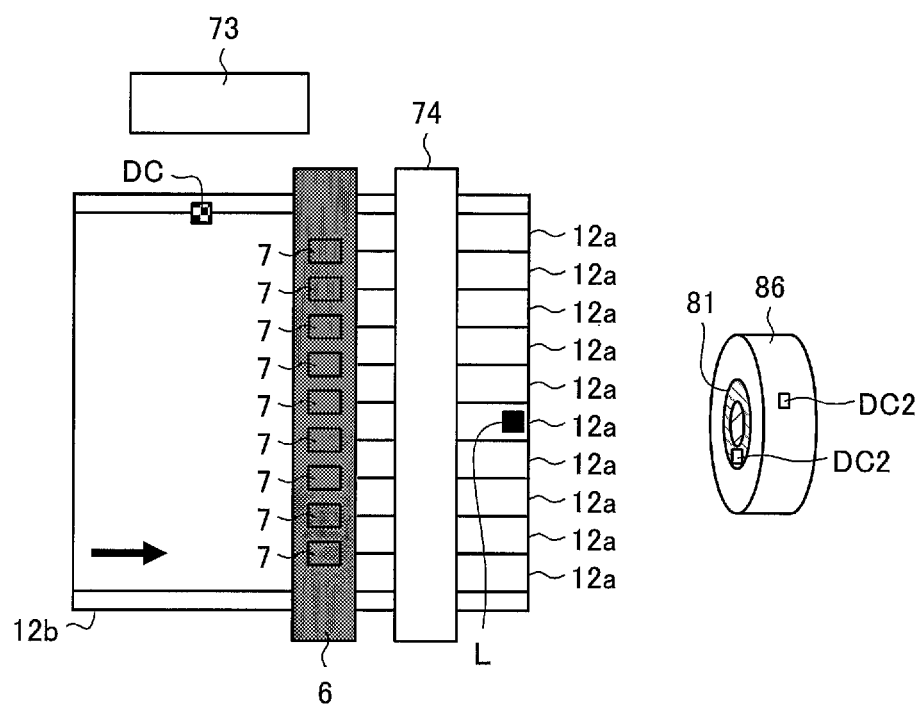
FIG. 10 is a diagram schematically illustrating a reading step, a mark providing step, and a wind-up step all included in a method for specifying the position of a defect in a separator.

FIG. 10 is a diagram schematically illustrating a reading step (defect information obtaining step), a determining step, a mark providing step, and a wind-up step all included in a method for specifying the position of a defect in a separator 12a. The separator original sheet 12b is wound off from the core 53 (see FIG. 8) at a fixed speed (for example, 80 m/min). A reading section 73 (defect information obtaining section) reads a defect code DC recorded at a portion on a widthwise side of the separator original sheet 12b to obtain defect information for the separator original sheet 12b (defect information obtaining step). The plurality of cutting devices 7, included in the slitting apparatus 6, cut the separator original sheet 12b lengthwise to prepare a plurality of separators 12a (slitting step).

<Defect Removing Step>

Next, a determining device 75 (determining section) determines on the basis of the defect code DC read by the reading section 73 that a separator among the plurality of separators which separator has the defect D is defective (defective film) (determining step). A mark providing device 74 then provides a mark L at a position corresponding to the defect D in the separator 12a, which is defective as the determining device 75 has determined (defect marking providing step). In a case where there are a plurality of defects D present, the determining device 75 determines that a plurality of separators 12a are defective. The mark L is preferably a label, so the mark providing device 74 is preferably a labeler.

The mark L may be, instead of a label, a mark drawn with a pen or a mark applied by an injector. The mark L may also be a thermolabel, which is printed by heating the separator 12a (made of resin). The mark L may also be provided by forming a hole in the separator 12a with use of a laser.

The plurality of separators 12a, prepared by slitting the separator original sheet 12b with use of the cutting devices 7, are each wound up around one of a plurality of cores 81 (wind-up step).

The mark providing device 74 then records information on the position of the defect D in the lengthwise direction of the separator original sheet 12b, which defect D is indicated by a defect code DC. The mark providing device 74 records such information as a defect code DC2 on (i) an outermost portion 86 of the separator 12a identified and wound up and/or (ii) the core 81.

Figure 11:
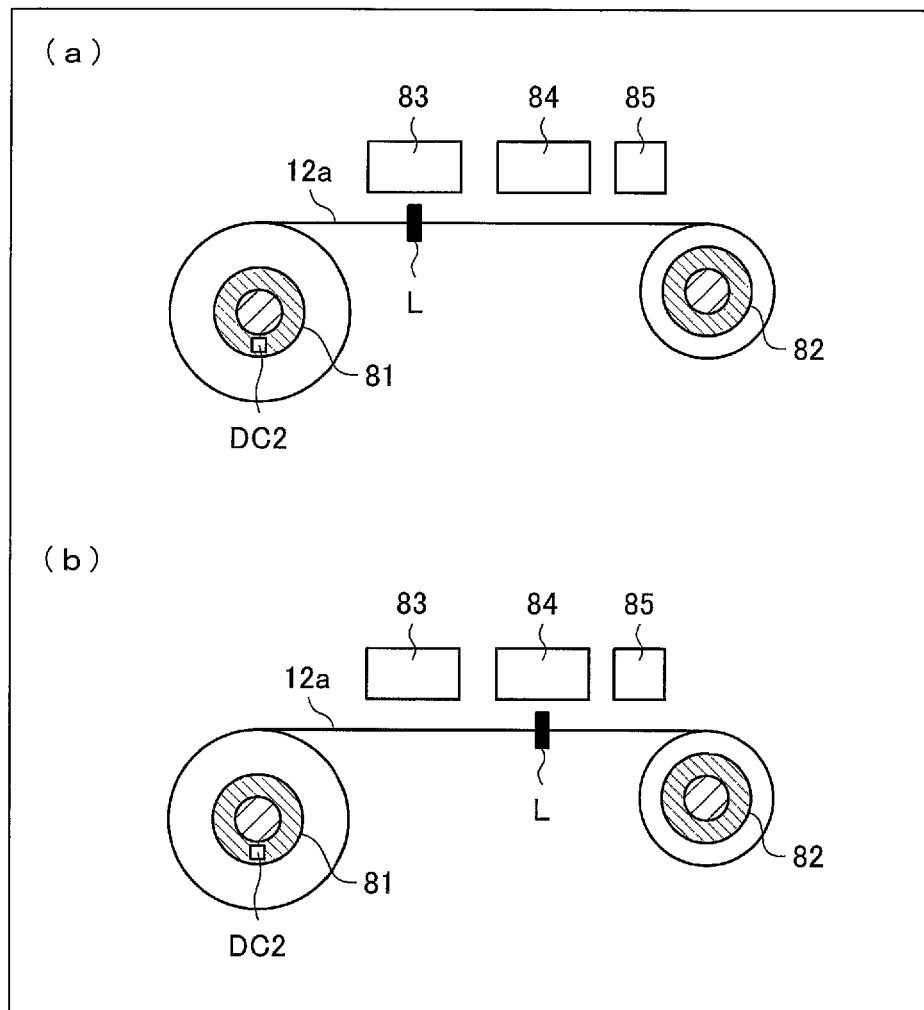
FIG. 11 provides diagrams schematically illustrating a mark sensing step and a defect removing step both included in a method for specifying the position of a defect in a separator.

FIG. 11 provides diagrams schematically illustrating a mark sensing step and a defect removing step both included in a method for specifying the position of a defect in a separator 12a. (a) of FIG. 11 is a diagram schematically illustrating the mark sensing step. (b) of FIG. 11 is a diagram schematically illustrating the defect removing step. First, a mark sensing device 83 reads a defect code DC2 recorded on the outermost portion 86 and/or core 81. The mark providing device 74 receives information read by the mark sensing device 83 and attaches a mark L to the separator 12a with the defect D present therein. The mark sensing step then starts an operation of winding off the separator 12a from the core 81 and winding up the heat-resistant separator 12a again around a core 82. Next, the mark sensing device 83, on the basis of information on the position of the defect D (indicated by the defect code DC2 read by the mark sensing device 83) in the lengthwise direction of the separator original sheet 12b, slows the above operation when the defect D has become close to the core 82.

The mark sensing device 83 then senses the mark L, which is attached to the position corresponding to the defect D in the separator 12a (mark sensing step). When the mark sensing device 83 has sensed the mark L, the mark sensing device 83 stops the operation of winding up the separator 12a again. Then, a defect removing device 84 cuts the separator 12a widthwise at (i) a position upstream of the defect D (which corresponds to the mark L) and (ii) a position downstream of the defect D, and removes the defect D from the separator 12a (defect removing step). The defect removing step may alternatively be carried out manually by an operator instead of the defect removing device 84. Then, a connecting device 85 connects two portions of the separator 12a that are separated from each other as the result of cutting the separator 12a (connecting step). The connecting step may alternatively be carried out manually by an operator instead of the connecting device 85. Next, the connecting device 85 resumes the operation of winding up the separator 12a again. The operation of winding off the separator 12a from the core 81 and winding up the separator 12a again around the core 82 is then completed. The two portions of the separator 12a, which result from dividing the separator 12a, may alternatively be left unconnected to be individually wound up around separate cores. In other words, the separator 12a may be wound up again in such a manner that that portion of the separator 12a which is downstream of the removed portion is wound up around the core 82, whereas that portion of the separator 12a which is upstream of the removed portion is wound up around another core.

Embodiment 2

Embodiment 1 is an example in which information on the position of a defect D present in a separator original sheet 12b is recorded at a widthwise end of the separator original sheet 12b. The present invention is, however, not limited to such a configuration, and may be configured such that information on the position of a defect D is recorded in an information storing device.

Figure 12:
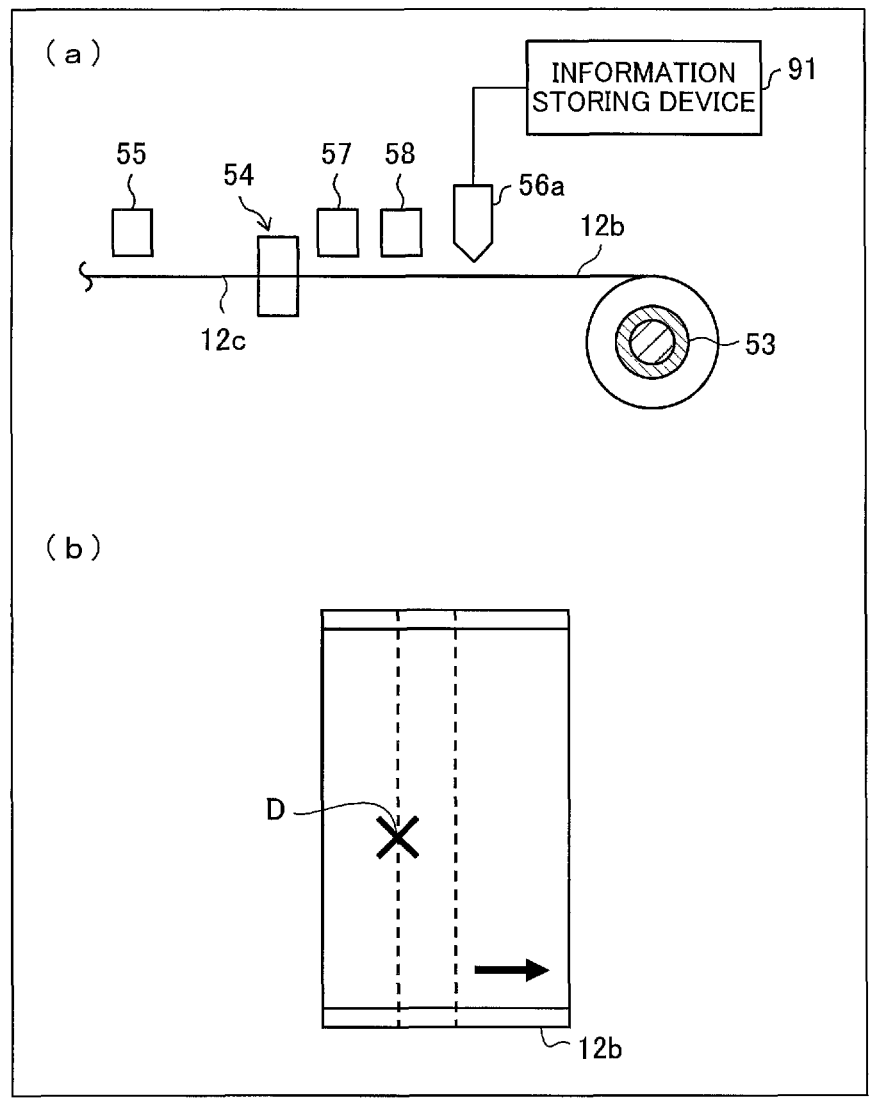
FIG. 12 provides diagrams schematically illustrating a defect detecting step and a defect information recording step both included in a method in accordance with Embodiment 2 for marking a defect in a separator original sheet.
Figure 13:
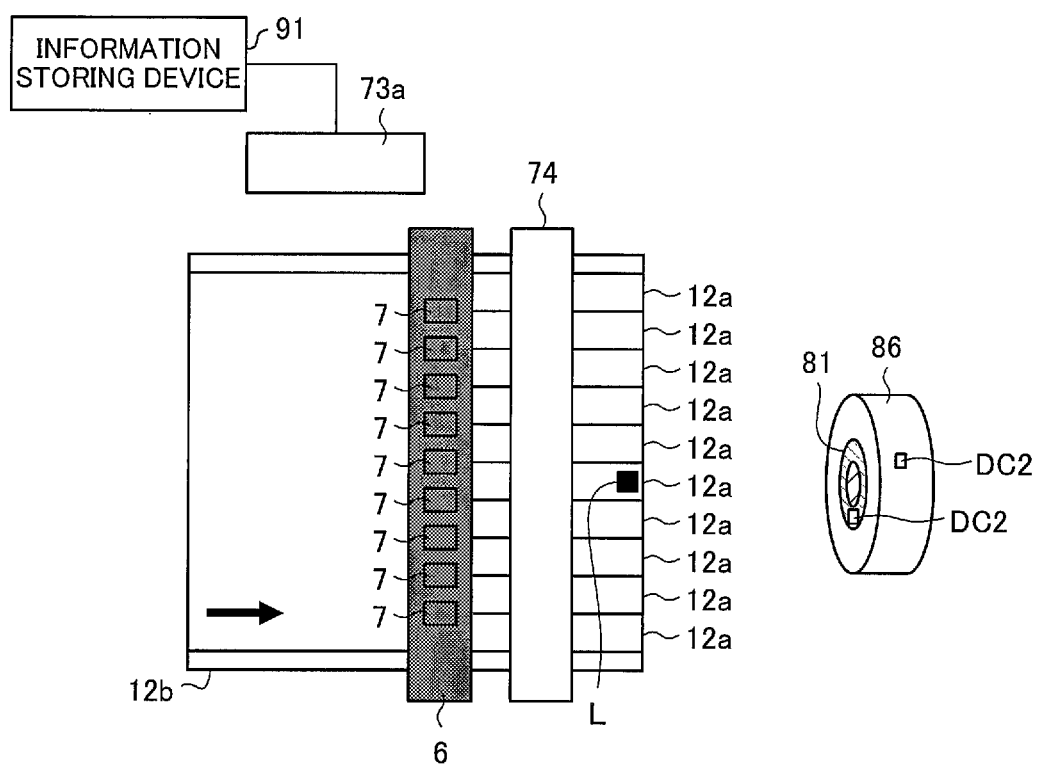
FIG. 13 is a diagram schematically illustrating a reading step, a mark providing step, and a wind-up step all included in a method for specifying the position of a defect in a separator.

FIG. 12 provides diagrams schematically illustrating a defect detecting step and a defect information recording step both included in a method in accordance with Embodiment 2 for marking a defect in a separator original sheet 12b. FIG. 13 is a diagram schematically illustrating a reading step, a mark attaching step, and a wind-up step all included in a method for specifying the position of a defect in a separator 12a. Any constituent element of Embodiment 2 that is identical to a corresponding constituent element described earlier for Embodiment 1 is assigned a common reference sign, and is not described in detail here.

A defect information recording device 56a (defect information recording section, separator original sheet producing apparatus) records, in an information storing device 91, positional information indicative of the lengthwise and widthwise positions of a defect D that is present in the separator original sheet 12c or 12b and that has been detected by the base material defect inspecting device 55, the coating defect inspecting device 57, or the pinhole defect inspecting device 58. A reading section 73a reads the positional information from the information storing device 91 (reading step).

Embodiment 3

Figure 14:
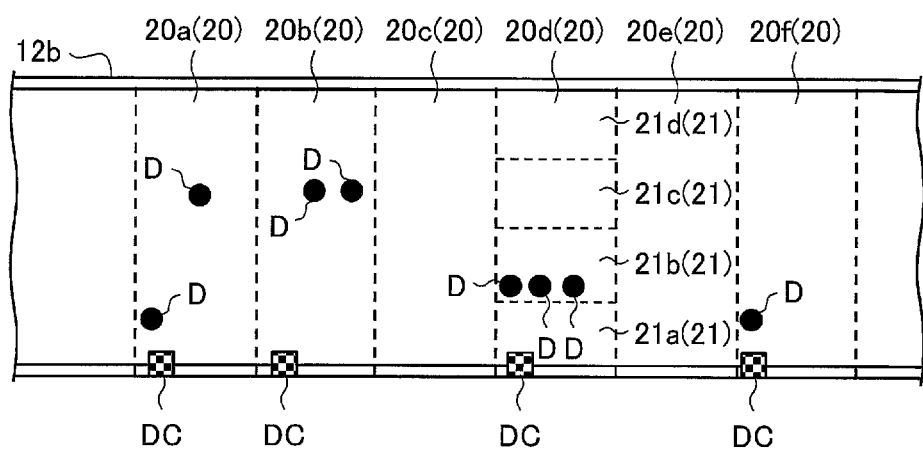
FIG. 14 is a plan view of a separator original sheet for illustration of where a defect code is recorded in a separator producing method in accordance with Embodiment 3.
Figure 15:
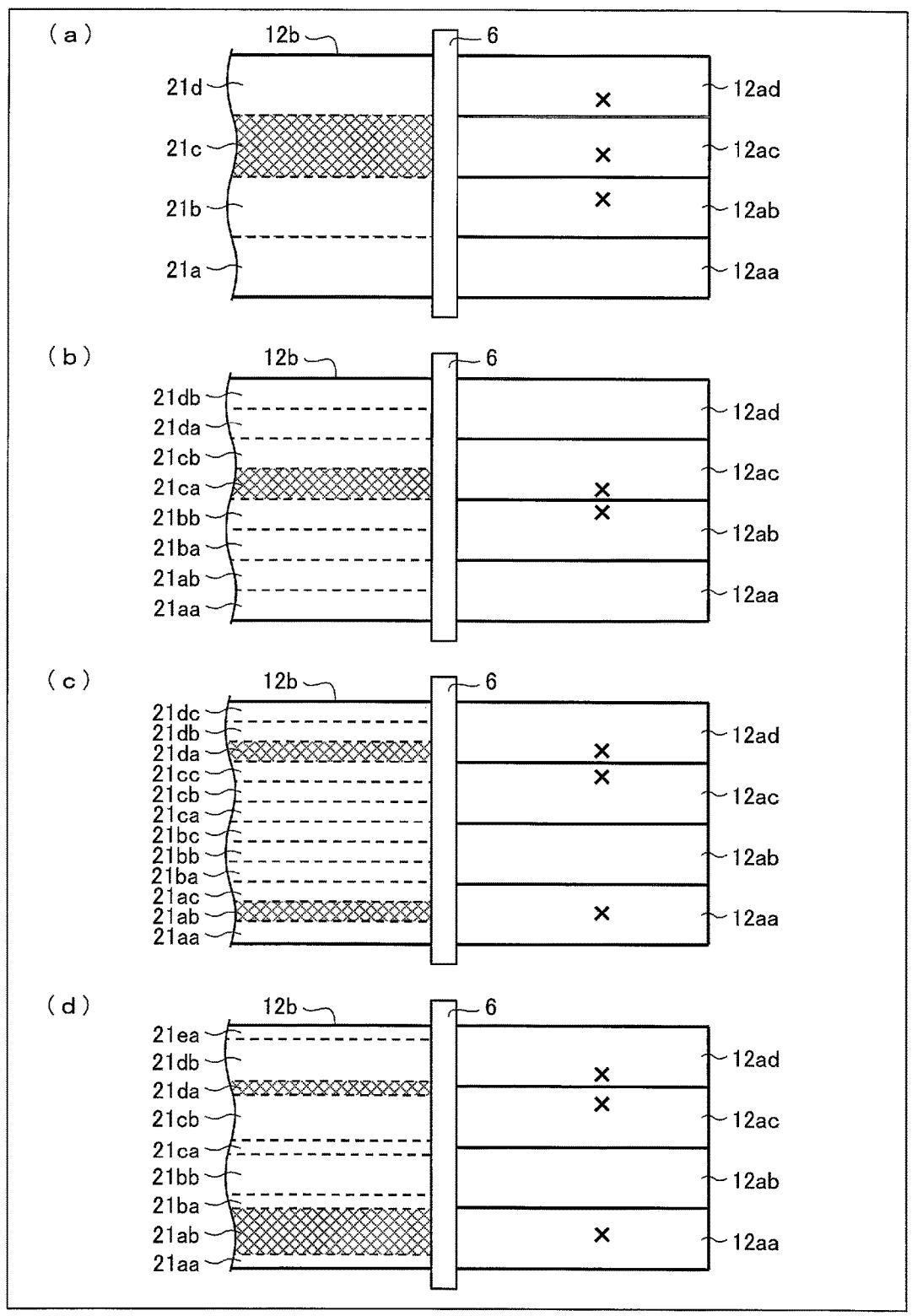
FIG. 15 provides diagrams each illustrating an example relationship between each divisional region having a defect, slit lines, and defective separators.

The following description will discuss another embodiment of the present invention with reference to FIGS. 14 and 15. Note that, for convenience of explanation, identical reference numerals are given to members which have respective functions identical with those described in Embodiment 1 or 2, and descriptions of the respective members are omitted.

In Embodiment 1, the defect information recording device 56 records a defect code DC at a portion of a separator original sheet 12b which portion corresponds to the position of a defect D in the longitudinal direction of the separator original sheet 12b. The defect information recording step 56, however, does not necessarily record a defect code DC in such a manner.

The following description will discuss how the defect information recording device 56 of Embodiment 3 records a defect code DC.

<Unit Region>

FIG. 14 is a plan view of a separator original sheet for illustration of where a defect code DC is recorded.

As illustrated in FIG. 14, the defect information recording device 56 of Embodiment 3 records (forms), for each unit region 20 having a predetermined length in the longitudinal direction of the separator original sheet 12b, a defect code DC indicative of any defect D in that unit region 20 (defect information recording step).

The unit region 20 can have a length of, for example, 250 mm in the longitudinal direction of the separator original sheet 12b.

FIG. 14 shows six example unit regions 20a to 20f arranged in the longitudinal direction of a separator original sheet 12b. FIG. 14 also shows a defect code DC recorded in correspondence with each of the unit regions 20a, 20b, 20d, and 20f, each of which has one or more defects D. FIG. 14 shows an example in which the defect information recording device 56 does not record a defect code DC in a unit region 20 having no defect D such as the unit regions 20c and 20e.

The defect information recording device 56 records, in a unit region 20 having a plurality of defects D such as the unit regions 20a and 20b, a single defect code DC indicative of, for example, information on the respective positions of the plurality of defects D.

Recording, in each unit region 20, a single defect code DC indicative of, for example, information on the respective positions of a plurality of defects D as described above makes it possible to reduce the number of recorded defect codes DC in comparison to a case of recording a single defect code DC for each defect D. This in turn makes it possible to simplify the production process.

<Information Included in Defect Code>

The defect information recording device 56 records a defect code DC indicative of detailed information such as (i) the number and/or type(s) of defects D in the unit region 20, (ii) the coordinates of the position of each defect D on the surface of the separator original sheet 12b, and (iii) the size of each defect D.

However, in a case where there are many defects D in a unit region 20, a single defect code DC cannot include detailed information on all of those defects D.

The defect information recording device 56 may thus alternatively be configured to divide a unit region 20 into a plurality of divisional regions 21 arranged in the width direction of the separator original sheet 12b and record a defect code DC indicative of simple information such as whether there is any defect D in each divisional region 21.

For example, as illustrated in FIG. 14 as an example, the defect information recording device 56 divides the unit region 20d, which has three defects D, into divisional regions 21a to 21d arranged in the width direction of the separator original sheet 12b and records a defect code DC indicative of information on whether there is any defect D in each of the divisional regions 21a to 21d. Specifically, the defect information recording device 56 records a defect code DC indicative of the following simple information: The divisional region 21a has no defect D. The divisional region 21b has defects D. The divisional region 21c has no defect D. The divisional region 21d has no defect D.

The above configuration makes it possible to reduce the amount of information to be included in a defect code DC. The divisional regions 21 illustrated in FIG. 14 are a mere example. The number of divisional regions 21 arranged in the width direction of a separator original sheet 12b and the width of each divisional region 21 can be set as appropriate.

The defect information recording device 56 may alternatively be configured to switch between a first mode, in which it records a defect code DC indicative of detailed information, and a second mode, in which it records a defect code DC indicative of simple information, in correspondence with the number of defects D in the unit region 20.

The above configuration makes it possible to, in a case where there is a restriction on the amount of information that can be included in a defect code DC, record a defect code DC indicative of information suitable under that restriction.

<Determining Step>

In Embodiments 1 and 2, the determining device 75 (determining section) identifies a single defective separator on the basis of a single defect D. A determining device 75 of Embodiment 3 carries out a determining step different from that carried out by the determining device 75 in Embodiment 1 or 2.

Embodiment 3 is configured such that (i) a reading section 73 reads a defect code DC recorded on a separator original sheet 12b, (ii) a slitting apparatus 6 slits the separator original sheet 12b along slit lines extending in the longitudinal direction of the separator original sheet 12b, and (iii) the determining device 75 determines on the basis of a single defect D that a first separator 12a actually having that defect D and a second separator 12a adjacent to the first separator 12a are defective (that is, determines those separators 12a as defective).

Then, a mark providing device 74 provides the first separator 12a (which actually has the defect D) with a mark L1 (first marking) indicative of the position of the defect D, and also provides a mark L2 (second marking) at a portion of the second separator 12a (adjacent to the first separator 12a) which portion corresponds to the mark L1 (defect marking providing step).

The second separator 12a is, in other words, a separator that corresponds to a region defined by slit lines (boundary lines) extending on the surface of the separator original sheet 12b in its longitudinal direction and that is provided with a mark L2 at a position opposite to the defect D across a slit line.

With the above configuration, even in a case where the slitting apparatus 6 has slit a separator original sheet 12b at positions different from desired slit positions, so that a defect D is not present in a first separator 12a in which the defect D would otherwise be present and that the defect D is present in a second separator 12a different from and adjacent to the first separator 12a, it is possible to determine that the second separator 12a is a defective separator 12a and thus to reduce the possibility of making a separator 12a having a defect D publicly available.

The defect marking providing step may be followed by a step of checking with use of a mark checking device whether the mark providing device 74 has provided a mark L at an appropriate position.

Embodiment 3 may further alternatively be configured such that (i) the reading section 73 reads a defect code DC indicative of simple information on whether each divisional region has one or more defects and that (ii) the determining device 75 determines on the basis of each divisional region 21 having at least one defect D that a first separator 12a including a divisional region 21 having a defect D and a second separator 12a different from and adjacent to the first separator 12a are defective.

The above configuration makes it possible to determine on the basis of simple information on whether there is any defect D in the divisional region 21 that the second separator 12a is defective.

This determination may be followed by a step of the defect removing device 84 cutting off a defective portion of each defective separator on the basis of marks L1 and L2 as illustrated in FIG. 11 (defect cutoff step).

The following description will discuss Embodiment 3 in greater detail with reference to drawings. The description below deals with a step of, in a case where the defect information recording device 56 has recorded a defect code DC indicative of simple information, the determining device 75 determining that a separator is defective.

FIG. 15 provides diagrams each illustrating an example relationship between each divisional region having a defect, slit lines, and defective separators. (a) of FIG. 15 illustrates a case of slitting a separator original sheet along slit lines arranged such that a single divisional region corresponds to a single separator. (b) of FIG. 15 illustrates a case of slitting a separator original sheet along slit lines arranged such that two divisional regions correspond to a single separator. (c) of FIG. 15 illustrates a case of slitting a separator original sheet along slit lines arranged such that three divisional regions correspond to a single separator. (d) of FIG. 15 illustrates a case of slitting a separator original sheet along slit lines each of which divides a divisional region. FIG. 15 omits defect codes DC. FIG. 15 shows "x" to indicate where a defect D in a divisional region can be present in a separator after the slitting step.

<Single Divisional Region Corresponding to Single Separator>

(a) of FIG. 15 shows the following example: The defect information recording device 56 records a defect code DC indicative of simple information for divisional regions 21a to 21d each having a width equal to that of a separator 12a. The reading section 73 reads the defect code DC. The slitting apparatus 6 slits the separator original sheet 12b along slit lines extending on the boundary lines between the divisional regions 21a to 21d to produce separators 12aa to 12ad corresponding respectively to the divisional regions 21a to 21d.

In a case where the slitting apparatus 6 slits a separator original sheet 12b along slit lines extending on the boundary lines between divisional regions 21 having a defect D as described above, displacement of the slit positions likely results in a defect being in a separator 12a that is different from and adjacent to a separator 12a in which the defect would otherwise be present.

In view of that, the determining device 75 of Embodiment 3 determines that a first separator 12a including a first divisional region 21 having a defect D is defective and that a second separator 12a is also defective, which second separator 12a is different from the first separator 12a and includes a second divisional region 21 adjacent to the first divisional region 21 via their boundary line.

More specifically, as illustrated in (a) of FIG. 15, in a case where the divisional region 21c has a defect D, the determining device 75 determines that the separator 12ac, which includes the divisional region 21c, is defective and that the separator 12ab, which includes the divisional region 21b adjacent to the divisional region 21c via their boundary line, and the separator 12ad, which includes the divisional region 21d adjacent to the divisional region 21c across their boundary line, are also defective separators.

A method for producing a separator 12a which method includes the determining step of Embodiment 3 makes it possible to appropriately determine that a separator 12a likely to have a defect as a result of displacement of slit positions is defective. This in turn makes it possible to reduce the risk of erroneously determining that a separator is non-defective when it is actually defective.

<Two Divisional Regions Corresponding to Single Separator>

(b) of FIG. 15 shows the following example: The defect information recording device 56 records a defect code DC indicative of simple information for divisional regions 21aa to 21db each having a width that is half the width of a separator 12a. The reading section 73 reads the defect code DC. The slitting apparatus 6 slits the separator original sheet 12b along slit lines extending on every other boundary line between the divisional regions 21aa to 21db. This makes it possible to produce a separator 12aa corresponding to the divisional regions 21aa and 21ab, a separator 12ab corresponding to the divisional regions 21ba and 21bb, a separator 12ac corresponding to the divisional regions 21ca and 21cb, and a separator 12ad corresponding to the divisional regions 21da and 21db.

The determining device 75 of Embodiment 3 determines that a first separator 12*a* including a first divisional region 21 having a defect D is defective and that a second separator 12*a* is also defective, which second separator 12*a* is different from the first separator 12*a* and includes a second divisional region 21 adjacent to the divisional region 21 via their boundary line.

More specifically, as illustrated in (b) of FIG. 15, in a case where the divisional region 21*ca* has a defect D, the determining device 75 determines that the separator 12*ac*, which includes the divisional region 21*ca*, is defective and that the separator 12*ab*, which includes the divisional region 21*bb* adjacent to the divisional region 21*ca* via their boundary line, is also defective.

As in the example illustrated in (a) of FIG. 15, in a case where the slitting apparatus 6 slits a separator original sheet 12*b* in such a manner that each separator 12*a* corresponds to a single divisional region 21, a defect D is likely present in either of the separators 12*a* on respective opposite sides of a separator 12*a* corresponding to a divisional region 21 having the defect D. This makes it necessary to determine that such separators 12*a* on the respective opposite sides are defective. This in turn results in determining for each defect D that three separators 12*a* are defective.

This is contrasted with the example illustrated in (b) of FIG. 15, in which a defect D is unlikely to be present in the separator 12*ad* out of the separators 12*ab* and 12*ad* on the respective opposite sides of the separator 12*ac*, which includes the divisional region 21*ca* having a defect D. This eliminates the need to determine that the separator 12*ad* is a defective separator 12. This in turn makes it possible to reduce the number of separators 12*a* that are determined as defective even though they actually have no defect D.

<Three Divisional Regions Corresponding to Single Separator>

(c) of FIG. 15 shows the following example: The defect information recording device 56 records a defect code DC indicative of simple information for divisional regions 21*aa* to 21 do each having a width that is one-third of the width of a separator 12*a*. The reading section 73 reads the defect code DC. The slitting apparatus 6 slits the separator original sheet 12*b* along slit lines extending on every three boundary lines between the divisional regions 21*aa* to 21*dc*. This makes it possible to produce a separator 12*aa* corresponding to the divisional regions 21*aa*, 21*ab*, and 21*ac*, a separator 12*ab* corresponding to the divisional regions 21*ba*, 21*bb*, and 21*bc*, a separator 12*ac* corresponding to the divisional regions 21*ca*, 21*cb*, and 21*cc*, and a separator 12*ad* corresponding to the divisional regions 21*da*, 21*db*, and 21*dc*.

In view of that, the determining device 75 of Embodiment 3 determines that a first separator 12*a* including a first divisional region 21 having a defect D is defective and that a second separator 12*a* is also defective, which second separator 12*a* is different from the first separator 12*a* and includes a second divisional region 21 adjacent to the first divisional region 21 via their boundary line.

More specifically, as illustrated in (c) of FIG. 15, in a case where the divisional region 21*da* has a defect D, the determining device 75 determines that the separator 12*ad*, which includes the divisional region 21*da*, is defective and that the separator 12*ac*, which includes the divisional region 21*cc* adjacent to the divisional region 21*da* via their boundary line, is also defective. In other words, in a case where the divisional region 21*da* has a defect D, the determining device 75 determines that the two separators 12*ac* and 12*ad*, which have been divided along the slit line extending on a boundary line of the divisional region 21*da*, are defective.

As in the example illustrated in (b) of FIG. 15, in a case where the slitting apparatus 6 slits a separator original sheet 12*b* in such a manner that each separator 12*a* corresponds to two divisional regions 21, a defect D is likely present in a separator 12*a* adjacent to a separator 12*a* corresponding to a divisional region 21 having the defect D. This makes it necessary to determine that such an adjacent separator 12*a* is defective. This in turn results in determining for each defect D that two separators 12*a* are defective.

This is contrasted with the example illustrated in (c) of FIG. 15, in which in a case where a defect D is present in a middle divisional region 21 among the three divisional regions 21 corresponding to a single separator 12*a*, it is only necessary to determine for each defect D that a single separator 12*a* is defective.

More specifically, as illustrated in (c) of FIG. 15, in a case where the divisional region 21*ab* has a defect D, the defect D is unlikely to be present in the separator 12*ab*, which is adjacent to the separator 12*aa* corresponding to the divisional region 21*ab*. This eliminates the need to determine that the separator 12*ab* is a defective separator 12. This in turn makes it possible to reduce the number of separators 12*a* that are determined as defective even though they actually have no defect D.

<Slit Lines Dividing Divisional Regions>

The respective examples of (a) to (c) of FIG. 15 are each an example in which the slitting apparatus 6 slits a separator original sheet 12*b* along slit lines extending on the boundary lines between divisional regions 21. The positional relationship between the boundary lines between divisional regions 21 and slit lines are, however, not limited to that.

(d) of FIG. 15 shows the following example: The defect information recording device 56 records a defect code DC indicative of simple information for narrow divisional regions 21*aa*, 21*ba*, 21*ca*, 21*da*, and 21*ea* (first divisional regions) and wide divisional regions 21*ab*, 21*bb*, 21*cb*, and 21*db* (second divisional regions) arranged alternately. The reading section 73 reads the defect code DC. The slitting apparatus 6 slits the separator original sheet 12*b* along slit lines each dividing a narrow divisional region to produce separators 12*aa* to 12*ad* each corresponding to a wide divisional region and two divisional parts of divisional regions.

In a case where a narrow divisional region has a defect D, two separators 12*a* each including a divisional part of that narrow divisional region are both likely to have the defect D.

In view of that, the determining device 75 of Embodiment 3 determines that two separators 12*a* each including a divisional part of a divisional region having a defect D are defective. In other words, the determining device 75 determines in a case where a divisional region through which a slit line extends has a defect D that two separators 12*a* overlapping with that divisional region are defective. The determining device 75 also determines in a case where a wide divisional region has a defect D that a single separator 12*a* including that wide divisional region is defective.

More specifically, as illustrated in (d) of FIG. 15, in a case where the divisional region 21*da* has a defect D, the determining device 75 determines that the two separators 12*ac* and 12*ad*, each of which includes a divisional part of the divisional region 21*da*, are defective. In other words, in a case where the divisional region 21*da* has a defect D, the determining device 75 determines that the two separators 12*ac* and 12*ad*, which have been divided along the slit line extending through the divisional region 21*da*, are defective. In a case where the divisional region 21*ab* has a defect D, the determining device 75 determines that the single separator 12*aa*, which includes the divisional region 21*ab*, is defective.

A method for producing a separator 12*a* which method includes the determining step of Embodiment 3 makes it possible to appropriately determine that a separator 12*a* likely to have a defect is defective. This in turn makes it possible to reduce the risk of erroneously determining that a separator is non-defective when it is actually defective.

In comparison to a case of slitting a separator original sheet 12*b* along slit lines each dividing a wide divisional region, slitting a separator original sheet 12*b* along slit lines each dividing a narrow divisional region less likely results in a defect being present in a divisional part of the divisional region. This makes it possible to reduce the number of separators that are determined as defective even though they actually have no defect.

Embodiment 4

Figure 16:
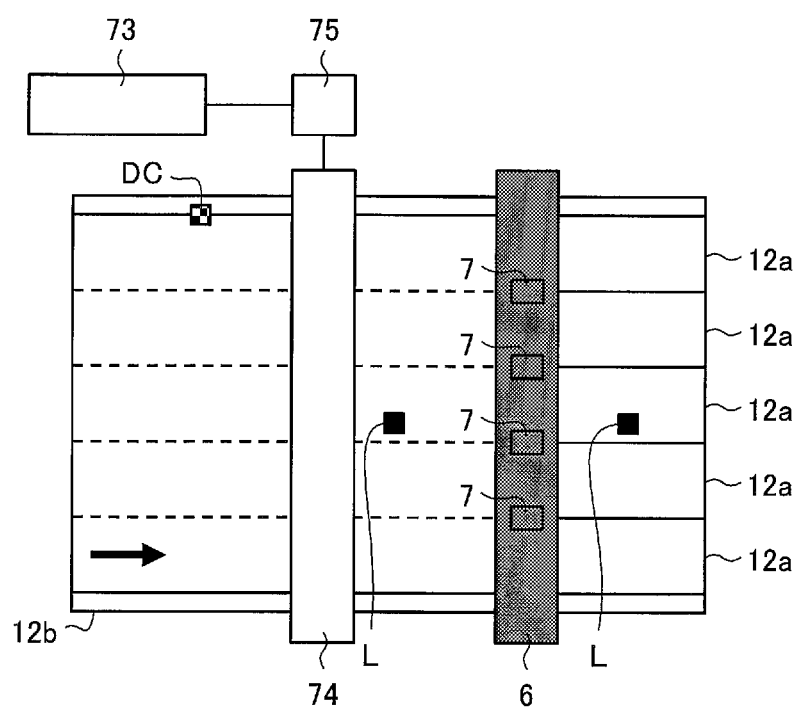
FIG. 16 is a diagram schematically illustrating a reading step, a mark providing step, and a wind-up step all included in a separator producing method in accordance with Embodiment 4.
Figure 17:
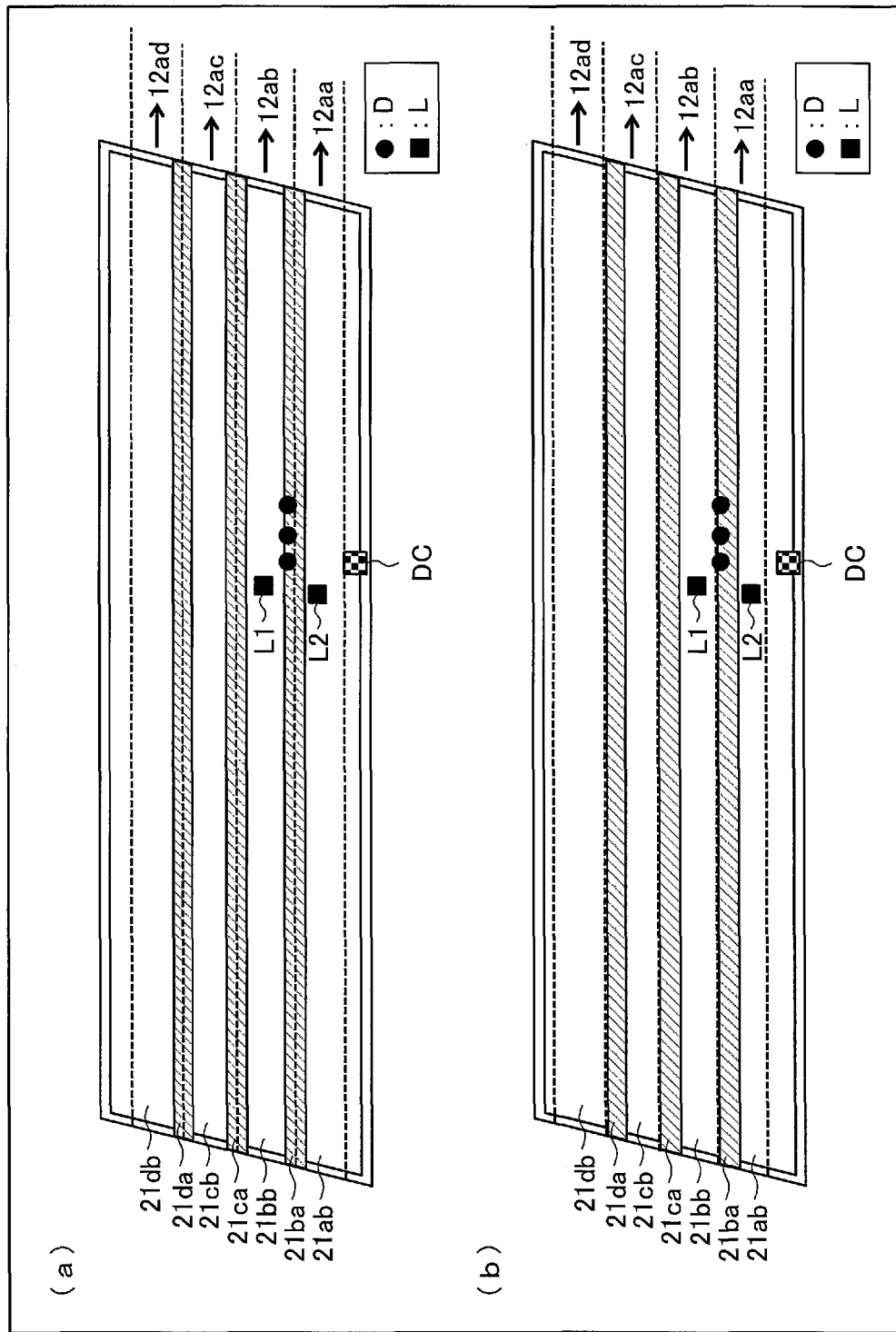
FIG. 17 provides perspective views of a separator original sheet or separators provided with marks at a position corresponding to defects.

The following description will discuss another embodiment of the present invention with reference to FIGS. 16 and 17. Note that, for convenience of explanation, identical reference numerals are given to members which have respective functions identical with those described in Embodiment 1, 2, or 3, and descriptions of the respective members are omitted.

FIG. 16 is a diagram schematically illustrating a reading step, a mark providing step, and a wind-up step all included in a method for specifying the position of a defect in a separator 12*a*.

The production method of Embodiment 3 includes a slitting step and a mark providing step in this order. These steps are, however, not necessarily carried out in the above order.

A production method of Embodiment 4 differs from the production method of Embodiment 3 in that the former includes a mark providing step and a slitting step in that order. The following description will discuss Embodiment 4 in greater detail.

As illustrated in FIG. 16, Embodiment 4 is configured such that (i) a reading section 73 reads a defect code DC recorded on a separator original sheet 12*b* (defect information obtaining step), (ii) a determining device 75 identifies, on the basis of the defect code DC, that portion of the separator original sheet 12*b* which will be a defective separator after the slitting step (determining step), and (iii) a mark providing device 74 provides a mark L to that portion of the separator original sheet 12*b* which will be a defective separator (original sheet defect marking providing step).

In a case where a mark L is provided to a separator 12*a* after the slitting step on the basis of information on the position of a defect D in the separator original sheet 12*b*, widthwise displacement of separators 12*a* during the slitting step may prevent the position of the defect D in the separator original sheet 12*b* from corresponding to the position of the defect D in a separator 12*a* after the slitting step. A mark L provided for a defect D may thus be displaced. In contrast, providing a mark L to a separator original sheet 12*b* before the slitting step on the basis of information on the position of a defect D in the separator original sheet 12*b* ensures that the mark L is correctly positioned to correspond to the defect D.

The marks L1 and L2 are preferably each so provided as not to overlap a slit line. This makes it possible to prevent a situation in which marks L1 and L2 have been cut during the slitting step and it is consequently difficult to determine whether a separator is defective.

FIG. 17 provides perspective views of a separator original sheet or separators provided with marks at a position corresponding to defects. (a) of FIG. 17 shows broken lines to indicate intended slit lines. (b) of FIG. 17 shows broken lines to indicate slit lines displaced from the intended positions.

FIG. 17 shows example separator original sheets 12*b* each provided with a defect code DC recorded by the defect information recording device 56 to indicate simple information for narrow divisional regions and wide divisional regions arranged alternately as illustrated in (d) of FIG. 15.

As illustrated in (a) of FIG. 17, in a case where a narrow divisional region 21*ba* has three defects D, the determining device 75 determines that two separators 12*ab* and 12*aa* each including a divisional part of the divisional region 21*ba* are defective. The mark providing device 74 provides a mark L1 to that portion of the separator original sheet 12*b* which corresponds to the separator 12*ab*, which has been determined as defective, and also provides a mark L2 to that portion of the separator original sheet 12 which corresponds to the separator 12*aa*, which has been determined as defective. The marks L1 and L2 are provided in the vicinity of the corresponding defects D.

The slitting apparatus 6 then slits the separator original sheet 12*b*, to which the marks L1 and L2 have been provided.

In a case where the slitting step and the mark providing step are carried out in that order as in the production method of Embodiment 3, the mark providing device 74 provides a mark L1 to the separator 12*ab* and a mark L2 to the separator 12*aa* after the slitting step. In a case where marks are provided to a separator original sheet 12*b* before the slitting step, those marks may be cut during the slitting step. However, providing marks L1 and L2 respectively to the separators 12*ab* and 12*aa* after the slitting step makes it possible to avoid such a risk.

As illustrated in (a) of FIG. 17, in a case where the separator original sheet 12*b* has been slit along the intended slit lines during the slitting step, the separator 12*ab* will have the defects D. However, as illustrated in (b) of FIG. 17, in a case where the separator original sheet 12*b* has been slit along slit lines displaced from the intended positions, the separator 12*aa* will have the defects D.

The production method of Embodiment 4 provides not only a mark L1 to a portion corresponding to the separator 12*ab*, but also a mark L2 to a portion corresponding to the separator 12*aa*. The production method of Embodiment 3 provides a mark L1 to the separator 12*ab* after the slitting step and also provides a mark L2 to the separator 12*aa*.

Thus, even in a case where slit lines have been displaced from the intended positions and the separator 12*aa* has defects D as a result, the separator 12*aa* as a defective separator can be prevented from being made publicly available.

(Other Aspects of the Present Invention)

In order to attain the above object, a separator original sheet producing method in accordance with an embodiment of the present invention includes the steps of: forming a separator original sheet; detecting a defect in the separator original sheet; and recording defect information including information on a first position of the defect which first position is a position in a width direction of the separator original sheet. The term "separator original sheet" refers to a wide separator that has not been slit.

The above feature involves recording defect information including information on a first position of a defect which first position is a position in the width direction of a separator original sheet. Referring to information recorded as such makes it possible to easily specify the position of a defect in a separator original sheet. This in turn makes it possible to easily remove a defect in a separator original sheet.

The separator original sheet producing method in accordance with an embodiment of the present invention may preferably be arranged such that the defect information further includes information on a second position of the defect which second position is a position in a longitudinal direction of the separator original sheet. The expression "longitudinal direction of the separator original sheet" refers to the direction in which a workpiece is conveyed during a process of producing a separator.

The above arrangement makes it possible to, on the basis of the information on the second position, easily find the defect when the separator original sheet is wound off.

The separator original sheet producing method in accordance with an embodiment of the present invention may preferably be arranged such that the defect information is recorded at a portion of the separator original sheet which portion corresponds to a second position of the defect which second position is a position in a longitudinal direction of the separator original sheet.

The above arrangement makes it possible to specify the second position of a defect on the basis of the position at which defect information has been recorded. Further, the defect information is recorded at a portion of the separator original sheet which portion corresponds to the second position of the defect. Thus, even in a case where the separator original sheet has been stretched lengthwise, the lengthwise position of the defect is substantially not displaced from the lengthwise position of the defect information. The lengthwise position of a defect is thus easily specifiable even in the case where the separator original sheet has been stretched lengthwise.

In order to attain the above object, a separator producing method in accordance with an embodiment of the present invention includes the steps of: (a) forming a separator original sheet; (b) detecting a defect in the separator original sheet; (c) recording defect information including information on a first position of the defect which first position is a position in a width direction of the separator original sheet; (d) cutting the separator original sheet having the defect, of which the information has been recorded in the step (c), in a longitudinal direction of the separator original sheet into a plurality of separators; (e) reading the information; and (f) on a basis of the information read in the step (e), providing at least one of the plurality of separators with a mark for specifying a position of the defect.

This feature involves providing, on the basis of the information read in the step (e), at least one of the plurality of separators with a mark for specifying the position of a defect. This makes it possible to easily remove a defective portion of a separator among the plurality of separators, prepared by slitting a separator original sheet, which separator has the defect.

The separator producing method in accordance with an embodiment of the present invention may preferably further include the steps of: (g) winding up the at least one of the plurality of separators, which at least one of the plurality of separators has been provided with the mark; (h) sensing the mark while carrying out an operation of winding off the at least one of the plurality of separators, which has been wound up in the step (g), and winding up the at least one of the plurality of separators again; and (i) in accordance with the sensing of the mark, stopping the operation and removing the defect.

The above arrangement, which involves removing a defect after the separator is wound up, eliminates the need to stop the winding and thus improves the working efficiency.

The separator producing method in accordance with an embodiment of the present invention may preferably be arranged such that in the step (i): the at least one of the plurality of separators is cut in the width direction at two positions opposite to each other in the longitudinal direction with the defect therebetween; the defect is removed; and cut parts of the separator are then connected.

The above arrangement makes it possible to remove a defect in a separator original sheet for separator production.

The separator producing method in accordance with an embodiment of the present invention may preferably be arranged such that in the step (c), the information is recorded at a widthwise end of the separator original sheet.

The above arrangement makes it possible to recognize a defective portion by simply reading information recorded at a widthwise end of a separator original sheet.

The separator producing method in accordance with an embodiment of the present invention may preferably be arranged such that in the step (c), the information is recorded in an information storing device.

The above arrangement makes it possible to recognize a defective portion by reading information recorded in an information storing device.

The separator producing method in accordance with an embodiment of the present invention may preferably be arranged such that the step (f) is carried out by attaching a label.

In order to attain the above object, a separator original sheet in accordance with an embodiment of the present invention includes: at a widthwise end thereof, information on a position of a defect in the separator original sheet which position is a position in a width direction.

In order to attain the above object, a separator original sheet producing apparatus in accordance with an embodiment of the present invention includes: a forming section configured to form a separator original sheet; a defect detecting section configured to detect a defect in the separator original sheet; and a defect information recording section configured to record defect information including information on a position of the defect which position is a position in a width direction of the separator original sheet.

The present invention is not limited to the embodiments, but can be altered by a skilled person in the art within the scope of the claims. An embodiment derived from a proper combination of technical means each disclosed in a different embodiment is also encompassed in the technical scope of the present invention.

REFERENCE SIGNS LIST

4 Heat-resistant layer
6 Slitting apparatus (slitting section)
7 Cutting device (cutting machine)
12 Separator (film)
12a Heat-resistant separator, separator (film)
12b Heat-resistant separator original sheet, separator original sheet (film original sheet)
12c Separator original sheet
54 Coating section (film original sheet producing apparatus)

55 Base material defect inspecting device (defect detecting section, film original sheet producing apparatus)
57 Coating defect inspecting device (defect detecting section, film original sheet producing apparatus)
58 Pinhole defect inspecting device (defect detecting section, film original sheet producing apparatus)
56, 56a Defect information recording device (defect information recording section, film original sheet producing apparatus)
73 Reading section
74 Mark providing device
75 Determining device (determining section)
81 Core
82 Core
83 Mark sensing device
84 Defect removing device
85 Connecting device
86 Outermost portion
91 Information storing device
D Defect
DC, DC2 Defect code
L Mark

The invention claimed is:

1. A film producing method, comprising the steps of:
(a) obtaining defect information including information on a position of a defect in a film original sheet, wherein the defect information indicates the presence or absence of defectiveness in each of a plurality of divisional regions arranged on a surface of the film original sheet in a width direction of the film original sheet;
(b) slitting the film original sheet along a slit line, extending in a longitudinal direction of the film original sheet, so as to produce a plurality of films, wherein each of the plurality of films includes at least one of the plurality of divisional regions or a portion of the at least one of the plurality of divisional regions; and
(c) carrying out defectiveness determination for the plurality of films on a basis of the defect information, wherein if at least one of the plurality of divisional regions or a portion thereof has the defect, the film including the at least one of the plurality of divisional regions or a portion thereof and another of said films adjacent to the film including the at least one of the plurality of divisional regions or a portion thereof are each considered to be a defective film.

2. A film producing apparatus, comprising:
a defect information obtaining section configured to obtain defect information including information on a position of a defect in a film original sheet, wherein the defect information indicates the presence or absence of defectiveness in each of a plurality of divisional regions arranged on a surface of the film original sheet in a width direction of the film original sheet;
a slitting section configured to slit the film original sheet along a slit line, extending in a longitudinal direction of the film original sheet, so as to produce a plurality of films, wherein each of the plurality of films includes at least one of the plurality of divisional regions or a portion of the at least one of the plurality of divisional regions, the at least one of the plurality of divisional regions including at least one border divisional region that is adjacent to or overlaps the slit line; and
a determining section configured to carry out defectiveness determination for the plurality of films on a basis of the defect information, wherein if the at least one border divisional region has the defect, one of said films including the at least one border divisional region or including a portion of the at least one border divisional region and another of said films adjacent across the slit line to the film including the at least one border divisional region or including the portion of the at least one border divisional region are each considered to be a defective film.

3. A film producing method, comprising the steps of:
(a) obtaining defect information including information on a position of a defect in a film original sheet, wherein the defect information indicates the presence or absence of defectiveness in each of a plurality of divisional regions arranged on a surface of the film original sheet in a width direction of the film original sheet;
(b) slitting the film original sheet along a slit line, extending in a longitudinal direction of the film original sheet, so as to produce a plurality of films, wherein each of the plurality of films includes at least one of the plurality of divisional regions or a portion of the at least one of the plurality of divisional regions, the at least one of the plurality of divisional regions including at least one border divisional region that is adjacent to or overlaps the slit line; and
(c) carrying out defectiveness determination for the plurality of films on a basis of the defect information, wherein
if the at least one border divisional region has the defect, one of said films including the at least one border divisional region or including a portion of the at least one border divisional region and another of said films adjacent across the slit line to the film including the at least one border divisional region or including the portion of the at least one border divisional region are each considered to be a defective film.

4. The film producing method according to claim 3, wherein:
in the step (b), the slit line extends on a boundary line between the plurality of divisional regions.

5. The film producing method according to claim 4, wherein:
in the step (b), the film original sheet is slit along the slit line, which extends on the boundary line between the plurality of divisional regions, in such a manner that the plurality of films correspond respectively to the plurality of divisional regions.

6. The film producing method according to claim 5, wherein:
in the step (b), the film original sheet is slit along the slit line in such a manner that the plurality of films each correspond to three of the plurality of divisional regions.

7. The film producing method according to claim 3, wherein:
in the step (b), the slit line divides one of the plurality of divisional regions; and
in the step (c), two films each including a divisional part of the at least one border divisional region are each considered to be a defective film.

8. The film producing method according to claim 7, wherein:
in the step (a), the defect information indicates presence or absence of defectiveness in each of alternating first divisional regions and second divisional regions, wherein the second divisional regions are wider than the first divisional regions;

in the step (b), the slit line divides one of the first divisional regions; and in the step (c), two films each including a divisional part of the at least one first divisional region are each considered to be a defective film.

9. The film producing method according to claim 3, further comprising the step of recording the defect information for each unit region having a predetermined length in the longitudinal direction of the film original sheet.

10. The film producing method according to claim 9, wherein in the step of recording the defect information, information on the presence or absence of defectiveness for each of the plurality of divisional regions in the unit region is recorded.

11. The film producing method according to claim 10, wherein in the step of recording the defect information, in correspondence with the number of defects in the unit region, switching is carried out between a first mode, in which the defect information recorded is at least one information item selected from the group consisting of (i) information on the number of defects in the unit region, (ii) information on a position of each of the defects, and (iii) information on a size of each of the defects, and a second mode, in which the defect information recorded is the information on the presence or absence of defectiveness for each of the plurality of divisional regions in the unit region.

12. The film producing method according to claim 3, further comprising the step of providing (i) the film actually having the defect with a first marking indicative of the position of the defect and (ii) the film adjacent to the film actually having the defect with a second marking at a position corresponding to the first marking.

13. The film producing method according to claim 3, further comprising the step of on the basis of the defect information, providing the film original sheet with (i) a first marking at a position corresponding to the film actually having the defect, the first marking indicating the position of the defect, and with (ii) a second marking at a position that corresponds to the film adjacent to the film actually having the defect and that is as shifted from the position of the first marking in the width direction, wherein in the step (b), the film original sheet provided with the first marking and the second marking is slit.

14. The film producing method according to claim 13, wherein in the step of the providing, the first marking and the second marking are so provided as not to coincide with the slit line.

15. The film producing method according to claim 3, further comprising the step of cutting off a portion of the defective film on the basis of the defect information.

* * * * *